US008685543B2

(12) United States Patent
Iwakuma et al.

(10) Patent No.: US 8,685,543 B2
(45) Date of Patent: *Apr. 1, 2014

(54) MATERIAL FOR ORGANIC ELECTROLUMINESCENT DEVICES AND ORGANIC ELECTROLUMINESCENT DEVICES MADE BY USING THE SAME

(75) Inventors: Toshihiro Iwakuma, Sodegaura (JP); Chishio Hosokawa, Sodegaura (JP); Hidetsugu Ikeda, Sodegaura (JP); Seiji Tomita, Sodegaura (JP); Takashi Arakane, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/484,854

(22) Filed: May 31, 2012

(65) Prior Publication Data
US 2012/0235129 A1  Sep. 20, 2012

Related U.S. Application Data

(63) Continuation of application No. 13/067,927, filed on Jul. 7, 2011, which is a continuation of application No. 10/504,477, filed as application No. PCT/JP03/02995 on Mar. 13, 2003, now Pat. No. 7,990,046.

(30) Foreign Application Priority Data

Mar. 15, 2002  (JP) ................ 2002-071398

(51) Int. Cl.
*H01L 51/54* (2006.01)
(52) U.S. Cl.
USPC ........ 428/690; 428/917; 313/504; 313/505; 313/506; 546/79; 546/81; 546/101; 548/418; 548/440; 257/40; 257/E51.05; 257/E51.026; 257/E51.032
(58) Field of Classification Search
USPC ............ 428/690, 917; 313/504, 505, 506; 546/79, 81, 101; 548/418, 434, 304.1; 257/40, E51.05, E51.026, E51.032
See application file for complete search history.

(56) References Cited

U.S. PATENT DOCUMENTS

| | | | |
|---|---|---|---|
| 2,944,058 A | 7/1960 | Kallischniggs | |
| 3,518,250 A | 6/1970 | Schumaker | |
| 4,480,096 A | 10/1984 | Fletcher | |
| 4,719,174 A | 1/1988 | Hirano et al. | |
| 4,769,292 A | 9/1988 | Tang et al. | |
| 4,819,057 A | 4/1989 | Naito et al. | |
| 5,059,863 A | 10/1991 | Tashiro et al. | |
| 5,104,749 A | 4/1992 | Sato et al. | |
| 5,391,681 A * | 2/1995 | Muhlebach et al. | 528/45 |
| 6,660,410 B2 | 12/2003 | Hosokawa | |
| 2001/0015614 A1* | 8/2001 | Taguchi | 313/483 |
| 2001/0046612 A1* | 11/2001 | Lee et al. | 428/690 |
| 2002/0028329 A1 | 3/2002 | Ise et al. | |
| 2002/0055014 A1 | 5/2002 | Okada et al. | |
| 2002/0146589 A1 | 10/2002 | Akiyama et al. | |
| 2003/0129448 A1* | 7/2003 | Lin et al. | 428/690 |
| 2003/0205696 A1 | 11/2003 | Thoms et al. | |
| 2004/0001967 A1* | 1/2004 | Lin | 428/690 |
| 2004/0110031 A1 | 6/2004 | Fukuda et al. | |
| 2012/0153267 A1 | 6/2012 | Matsuura et al. | |

FOREIGN PATENT DOCUMENTS

| | | |
|---|---|---|
| EP | 1 205 527 A1 | 5/2002 |
| JP | 03-200889 | 9/1991 |
| JP | 07-138561 | 5/1995 |
| JP | 08-012600 | 1/1996 |
| JP | 8-12430 | 2/1996 |
| JP | 08-239655 | 9/1996 |
| JP | 09-118708 | 5/1997 |
| JP | 10-226785 | 8/1998 |
| JP | 11-144876 A | 5/1999 |
| JP | 2000-75519 | 3/2000 |
| JP | 2000-169448 | 6/2000 |
| JP | 2000-260565 A | 9/2000 |
| JP | 2000-264880 A | 9/2000 |
| JP | 2000-268961 A | 9/2000 |
| JP | 2000-290644 A | 10/2000 |
| JP | 2000-344780 | 12/2000 |
| JP | 2001-160489 | 6/2001 |
| JP | 2001-247858 A | 9/2001 |
| JP | 2001-284051 A | 10/2001 |
| JP | 2002-50483 | 2/2002 |
| JP | 4140986 B2 | 8/2008 |
| KR | 1985-0000449 | 8/1983 |
| WO | 01/19939 A1 | 3/2001 |
| WO | 01/72927 A1 | 4/2001 |

OTHER PUBLICATIONS

Catalan, et al., On the TICT Mechanism of 9,9'-Biaryl Compounds, 1998, European Journal of Organic Chemistry , vol. 8, pp. 1697-1704.*
Rebek et. al., Passive Template Effects and Active Acid-Base Involvement in Catalysis of Organic Reactions, 1995, Chem. Eur. J., vol. 1, No. 3, pp. 183-192.*
Gilman, H., et al., "Some Aromatic and Heterocyclic Derivatives of Carbazole", Journal of Organic Chemistry, vol. 22, pp. 226-227 (1957).
Bai, F., et al., "Study of phtophysical processes in N-(2-pyridine)carbazole", Journal of Photochemistry and Photobiology, Part A: (Chemistry), vol. 63, pp. 187-194 (1992).
Avendano, C., et al., "The Problem of the Existence of C(Ar)—H•••N Intramolecular Hydrogen Bonds in a Family of 9-Azaphenyl-9H-carbazoles", Journal of the Chemical Society, Perkin Transactions 2, pp. 1547-1555 (1993).

(Continued)

*Primary Examiner* — Gregory Clark
(74) *Attorney, Agent, or Firm* — Oblon, Spivak, McClelland, Maier & Neustadt, L.L.P.

(57) ABSTRACT

A material for electroluminescent devices which comprises a compound in which a heterocyclic group having nitrogen is bonded to carbazolyl group and an organic electroluminescent device having at least one organic thin film layer which is sandwiched between the cathode and the anode and contains the above material in at least one layer, are provided. The material can provide organic electroluminescent devices emitting bluish light with a high purity of color. The organic electroluminescence device uses the material.

22 Claims, No Drawings

(56) References Cited

OTHER PUBLICATIONS

Boyer, G., et al., "Synthesis and Structure of New Hosts Related to 9,9'-Bianthryl", Journal of Chemical Society, Perkin Transactions 2, vol. 4, pp. 757-766, XP-002358146 (1993).

Huc, I., et al., "Role of Geometrical Factors in Template Effects," Journal of the American Chemical Society, vol. 116, pp. 10296-10297 (1994).

Mo, Y., et al., "Photophysical processes of some carbazole derivatives", Journal of Photochemistry and Photobiology A: Chemistry, vol. 92, pp. 25-27, XP-002358149 (1995).

Pieters, R., et al., "Passive Template Effects and Active Acid-Base involvement in Catalysis of Organic Reactions", Chem. Eur. J., vol. 1, No. 3, pp. 183-192, XP-002358150 (1995).

Herbich, J., et al., "Phosphorescent intramolecular charge transfer triplet states", Chemical Physics Letters, vol. 262, pp. 633-642 (1996).

Catalan, J., et al., "On the TICT Mechanism of 9,9'-Biaryl Compounds", Eur. J. Org. Chem., pp. 1697-1704, XP-002358148 (1998).

Grigalevicius, S., et al., "Hole-transporting molecular glasses based on carbazole and diphenylamine moieties", Materials Chemistry and Physics, vol. 72, No. 3, pp. 395-400, XP-002980841 (2001).

Jenekhe, S., et al., "New Conjugated Polymers with Donor-Acceptor Architectures: Synthesis and Photophysics of Carbozole-Quinoline and Phenothiazine-Quinoline Copolymers and Oligomers Exhibiting Large Intramolecular Charge Transfer", Macromolecules, vol. 24, No. 21, pp. 7315-7324 (2001).

Etori, H., et al., "Design of Multilayer Structure for UV Organic Light-Emitting Diodes Based on 2-(2-Naphthyl)-9,9'-spirobifluorene", Japanese Journal of Applied Physics, vol. 46, No. 8A, pp. 5071-5075 (2007).

Kusterer, J.M., "What Wavelength Goes With a Color?", Atmospheric Science Data Center, [online], retrieved from the internet, URL: http://eosweb.larc.nasa.gove/EDDOCS/Wavelengths_for_Colors.html>, Sep. 28, 2007, [retrieved on Aug. 21, 2008].

Andrzej Kapturkiewicz, et al., Intramolecular Radiative and Radiationless Charge Recombination Processes in Donor-Acceptor Carbazole Derivatives, *J. Phys. Chem. A.*, 1997, 101, 2332-2344.

Stephen T. Wellinghoff, et al., Synthesis and Characterization of Carbazole Polymers Exhibiting Large Nonlinear Absorption and Refractive Index, *Synthetic Metals*, 41-43 (1991) 3203-3207.

Eri Matsuda et al., "Photochemical Conversion of Anti-9-Methylcarbazole-3-Carbaldehyde Diphenylhydrazone to its Syn-Isomer and an Indazole," *Chemistry Letters*, pp. 1129-1132 (1992).

M.A. Baldo et al., "Transient Analysis of Organic Electrophosphorescence. II. Transient Analysis of Triplet-Triplet Annihilation," *Physical Review B*, vol. 62, No. 16, pp. 10967-10977 (Oct. 15, 2000).

Request for Trial and Argument in corresponding Korean Patent No. 0957288 (Jun. 25, 2013).

\* cited by examiner

MATERIAL FOR ORGANIC ELECTROLUMINESCENT DEVICES AND ORGANIC ELECTROLUMINESCENT DEVICES MADE BY USING THE SAME

This is a continuation application of U.S. application Ser. No. 13/067,927, filed Jul. 7, 2011, which is a continuation application of U.S. application Ser. No. 10/504,477, filed Aug. 12, 2004, which is a 371 of PCT/JP03/02995 filed on Mar. 13, 2003.

TECHNICAL FIELD

The present invention relates to a material for organic electroluminescent devices (organic EL devices) and organic EL devices made by using the material and, more particularly, to organic EL devices emitting bluish light with a high purity of color.

BACKGROUND ART

Organic EL devices which utilize organic substances are expected to be useful for application as an inexpensive full color display device of the solid light emission type having a great size, and various developments on the organic EL devices are being conducted. In general, an organic EL device has a construction comprising a pair of facing electrodes and a light emitting layer sandwiched between the electrodes.

The light emission of the organic EL device is a phenomenon in which, when an electric field is applied across the two electrodes, electrons are injected from the cathode side and holes are injected from the anode side, the electrons recombine with the holes in the light emitting layer to induce an excited state, and then, when the excited state returns to the original state, it emits energy as light.

As the light emitting material, chelate complexes such as tris(8-quinolinolato)aluminum, coumarine derivatives, tetraphenyl-butadiene derivatives, bisstyrylarylene derivatives and oxadiazole derivatives are known. It has been reported that these light emitting materials emit light in the visible region of blue to red, and it is expected that color display elements can be obtained by using these light emitting materials (see, for example, Japanese Patent Application Laid-Open Nos. Heisei 8(1996)-239655, Heisei 7(1995)-138561 and Heisei 3(1991)-200289).

Although the practical use of displays using organic EL devices recently started, the full color display device is still under development. In particular, an organic EL device which emits bluish light with excellent purity of color and great efficiency of light emission has been desired.

To overcome the above problems, for example, a device in which a phenylanthracene derivative is used as the material emitting blue light is disclosed in Japanese Patent Application Laid-Open No. Heisei 8(1996)-12600. The phenylanthracene derivative is used as the material emitting blue light and, in general, used as a laminate of a layer of the material emitting blue light with a layer of a complex of tris(8-quinolinolato) aluminum (Alq). However, the efficiency of light emission, the life and the purity of blue light are insufficient for the practical application. Japanese Patent Application Laid-Open No. 2001-160489 discloses a device in which an azafluoranthene compound is added to the light emitting layer. However, this device emits yellow to green light and cannot emit blue light having a sufficiently high purity of color.

SUMMARY OF THE INVENTION

The present invention has been made to overcome the above problems and has an object of providing a material for organic EL devices which emits bluish light with a high purity of light and an organic EL device utilizing the material.

As the result of intensive studies by the present inventors to achieve the above object, it was found that an organic EL device emitting bluish light with a high purity of light could be obtained by using a compound in which a heterocyclic group having nitrogen was bonded to carbazolyl group as the host material. The present invention has been completed based on this knowledge.

The present invention provides a material for organic EL devices which comprises a compound represented by following general formula (1):

$$(Cz\text{-})_n M_m \quad (1)$$

wherein Cz represents a substituted or unsubstituted carbazolyl group, M represents a substituted or unsubstituted heteroaromatic cyclic group having 2 to 40 carbon atoms and nitrogen atom, n and m each represent an integer of 1 to 3, a plurality of Cz may represent different groups when n represents 2 or 3, a plurality of M may represent different groups when m represents 2 or 3, and M does not represent triazine group when n represents 3 and m represents 1.

The present invention also provides an organic EL device which comprises a cathode, an anode and an organic thin film layer comprising at least one layer and sandwiched between the cathode and the anode, wherein at least one layer in the organic thin film layer contains a material for organic EL devices described above. In the organic thin film layer, a light emitting layer, an electron transporting layer or a hole transporting layer may contain the above material for organic EL devices.

THE MOST PREFERRED EMBODIMENT TO CARRY OUT THE INVENTION

The material for organic EL devices of the present invention comprises a compound represented by the following general formula (1):

$$(Cz\text{-})_n M_m \quad (1)$$

Cz represents a substituted or unsubstituted carbazolyl group, M represents a substituted or unsubstituted heteroaromatic cyclic group having 2 to 40 carbon atoms and nitrogen atom, n and m each represent an integer of 1 to 3, a plurality of Cz may represent different groups when n represents 2 or 3, a plurality of M may represent different groups when m represents 2 or 3, and M does not represent triazine group when n represents 3 and m represents 1.

Examples of the heteroaromatic cyclic group having nitrogen represented by M include groups derived from pyridine, pyrimidine, pyrazine, triazine, aziridine, azaindolidine, indolidine, imidazole, indole, isoindole, indazole, purine, pteridine, β-carboline, naphthylidine, quinoxaline, quinazoline, phenothiazine, acridine, phenanthroline and phenazine.

Examples of the substituent to the groups represented by Cz or M in general formula (1) include halogen atoms such as chlorine atom, bromine atom and fluorine atom; carbazole group, hydroxyl group, substituted or unsubstituted amine groups, nitro group, cyano group, silyl group, trifluoromethyl group, carbonyl group, carboxyl group, substituted or unsubstituted alkyl groups, substituted or unsubstituted alkenyl groups, substituted or unsubstituted arylalkyl groups, substituted or unsubstituted aromatic groups, substituted or unsubstituted heteroaromatic heterocyclic groups, substituted or unsubstituted aralkyl groups, substituted or unsubstituted aryloxy groups and substituted or unsubstituted alkyloxyl groups. Among these groups, fluorine atom, phenyl group, naphthyl group, pyridyl group, pyrazyl group, pyrimidyl group, cyano group, substituted or unsubstituted alkyl groups and substituted or unsubstituted aralkyl groups are preferable.

It is preferable that the compound represented by general formula (1) used in the present invention is a compound represented by any one of the following general formulae (2) to (10).

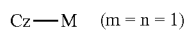
(2)

(3)

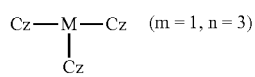
(4)

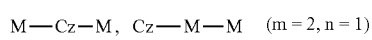
(5)

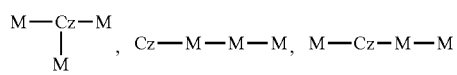
(6)

(m = 3, n = 1)

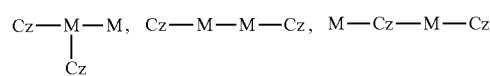
(7)

(m = 2, n = 2)

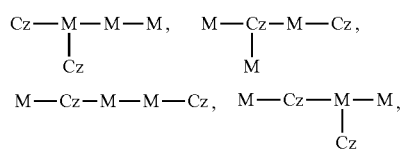
(8)

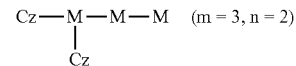

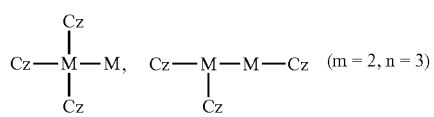
(9)

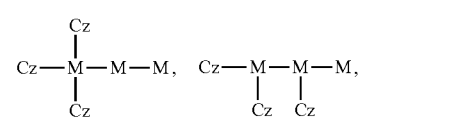
(10)

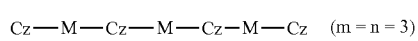

Specific examples of the compound represented by general formula (1) used in the present invention are shown in the following. However, the compound is not limited to the compounds shown in the following.

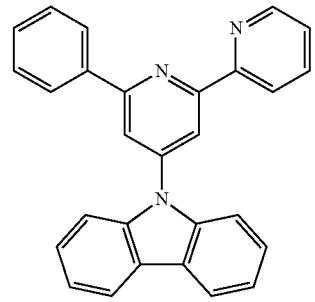
(A1)

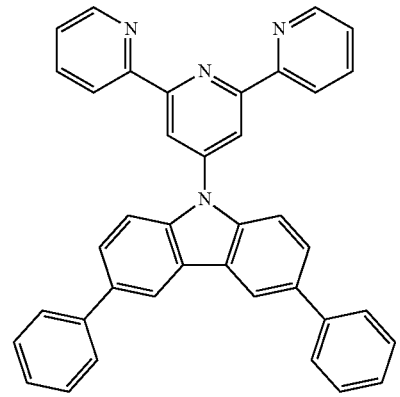
(A2)

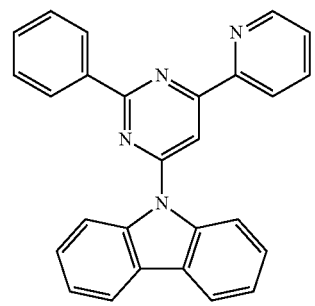
(A3)

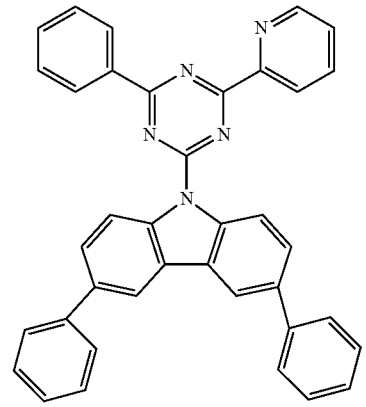
(A4)

(A5) 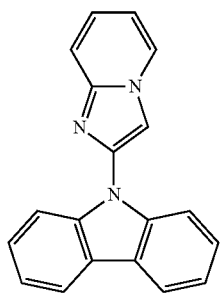
(A6) 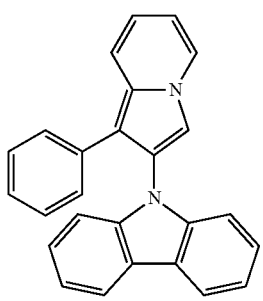
(A7) 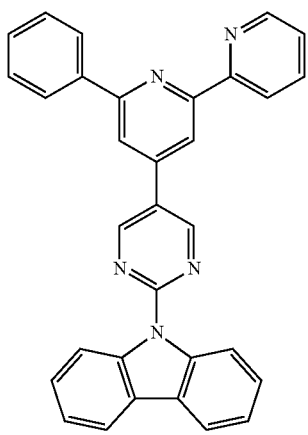
(A8) 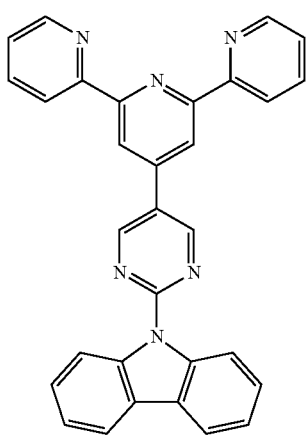
(A9) 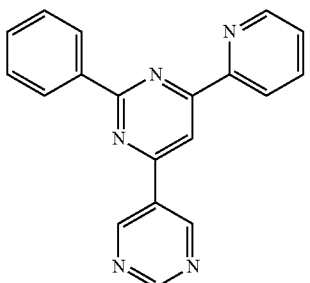
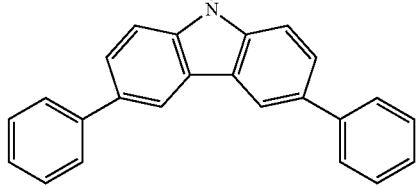
(A10) 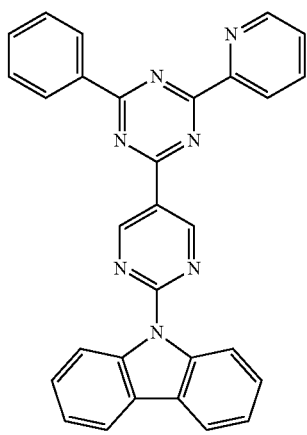
(A11) 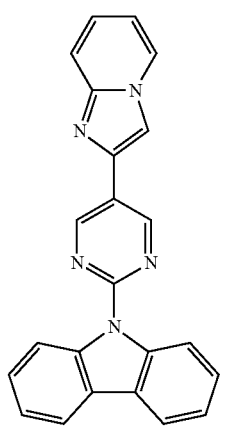

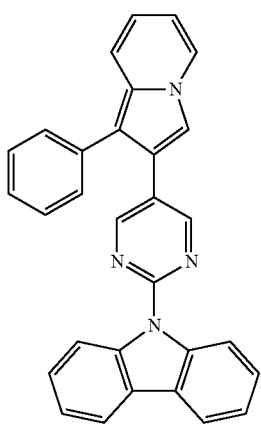
(A12)
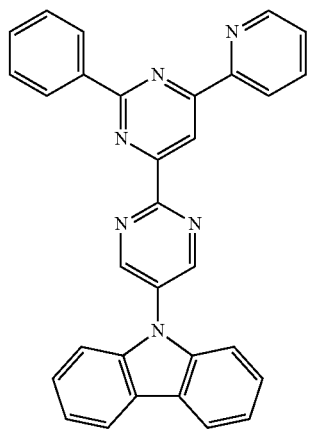
(A15)
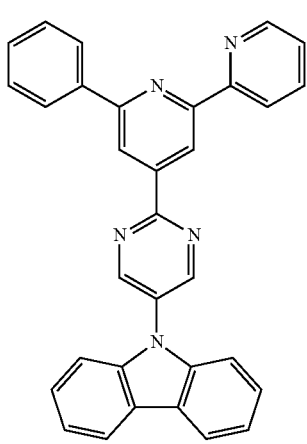
(A13)
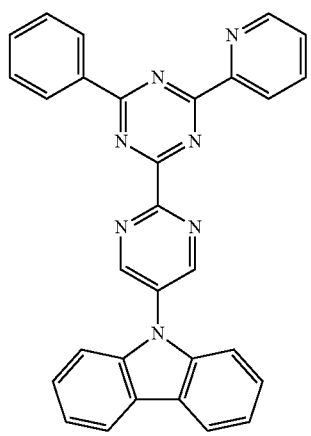
(A16)
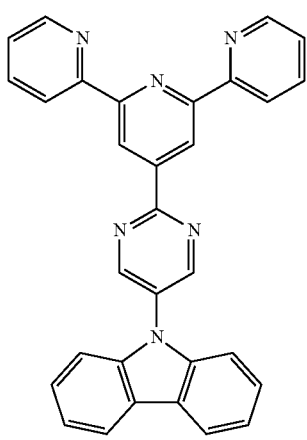
(A14)
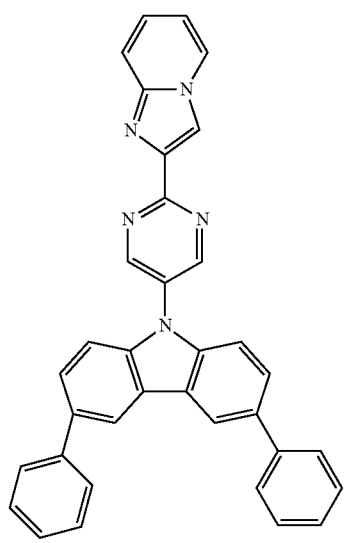
(A17)

(A18)

(A19)

(A20)

(A21)

(A22)

(A23)

(A24)

(A25)

(A26) 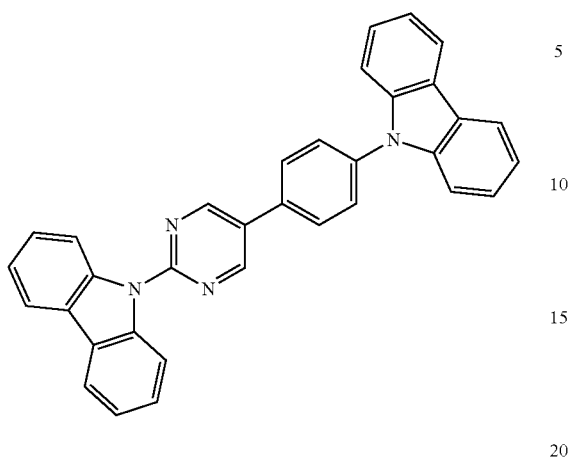
(A27) 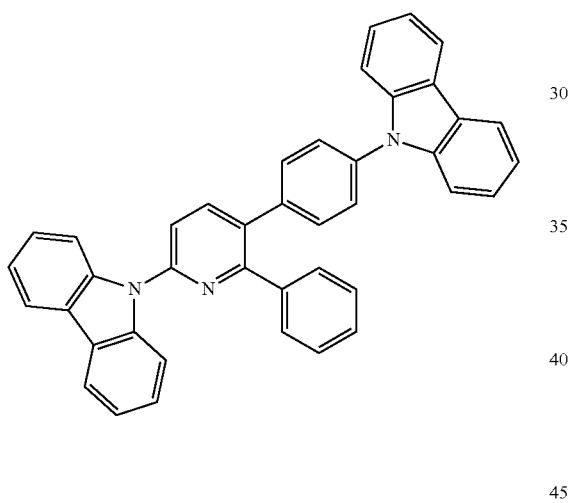
(A28) 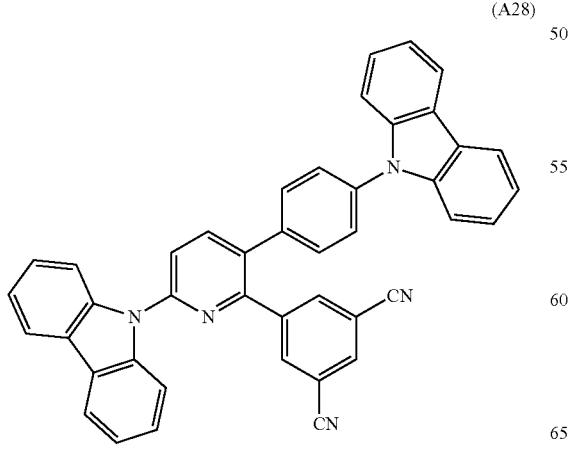
(A29) 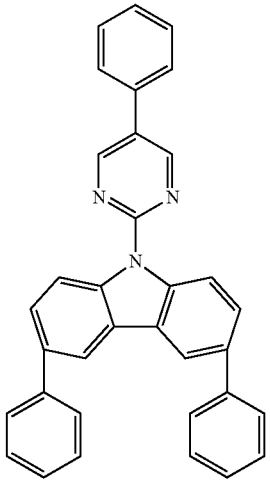
(A30) 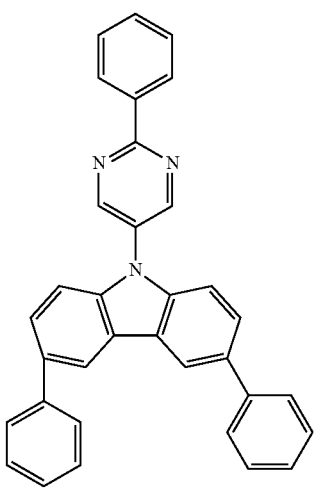
(A31) 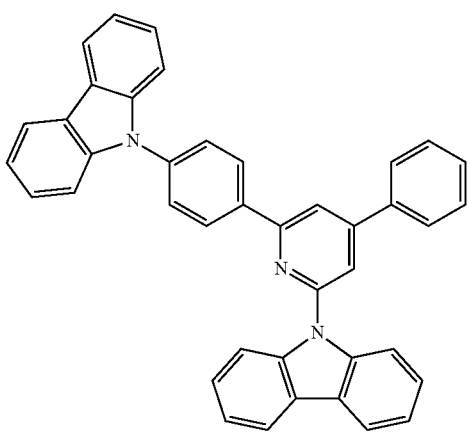

(A32) 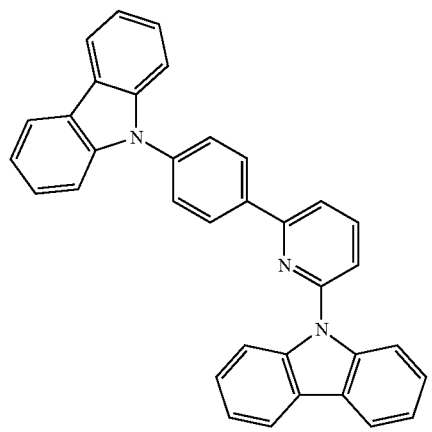
(A35) 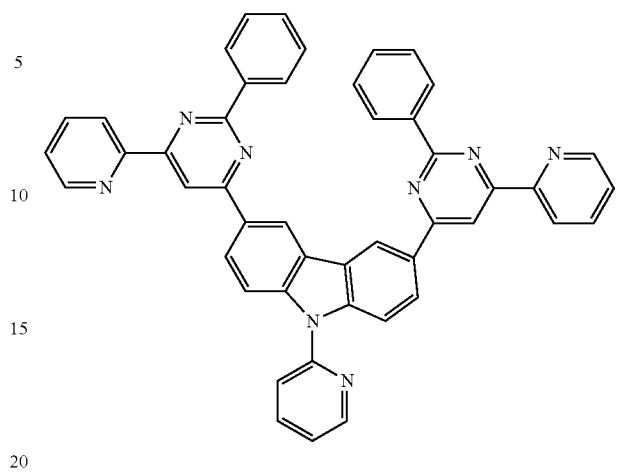
(A33) 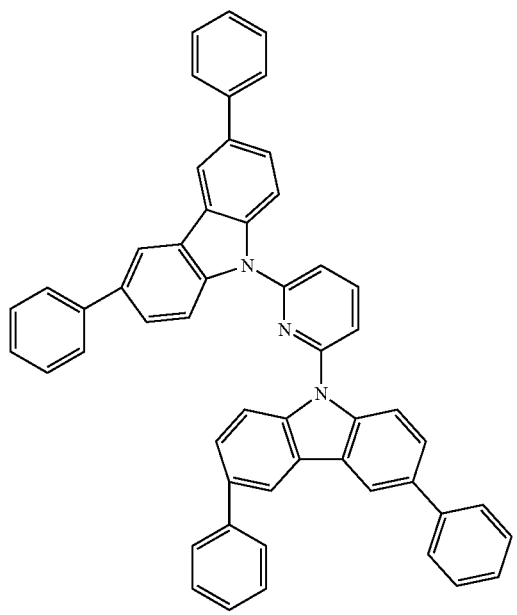
(A36) 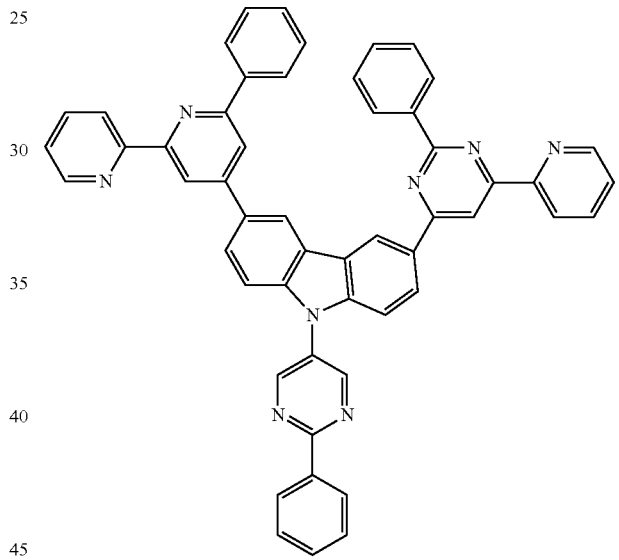
(A34) 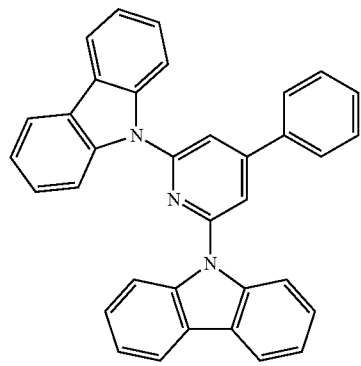
(A37) 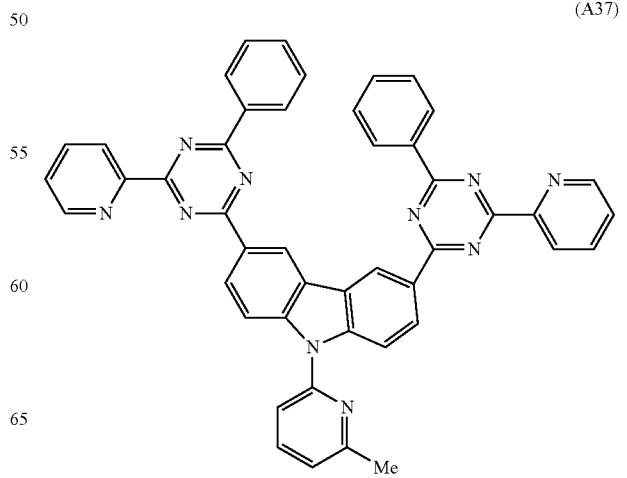

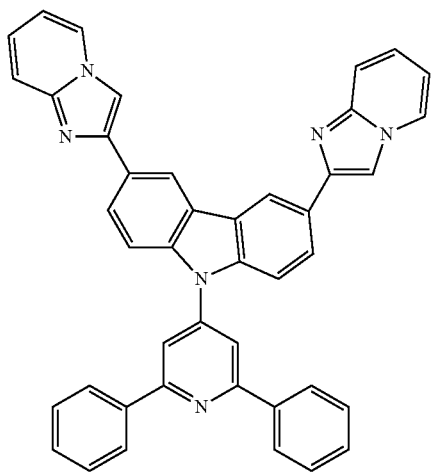
(A38)
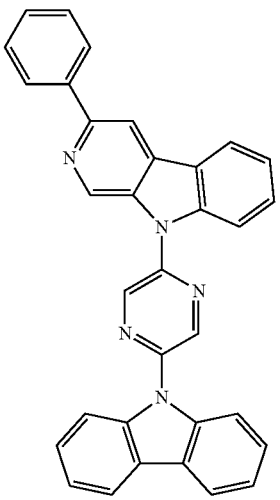
(A41)
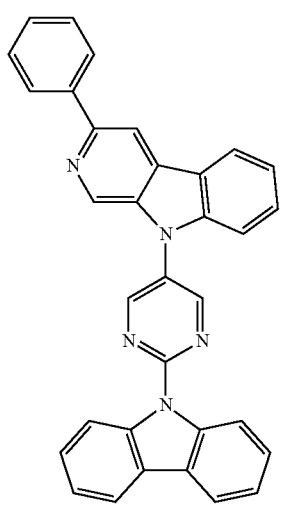
(A39)
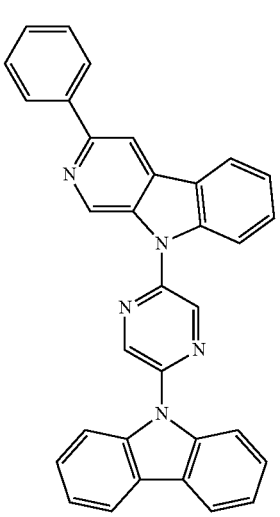
(A42)
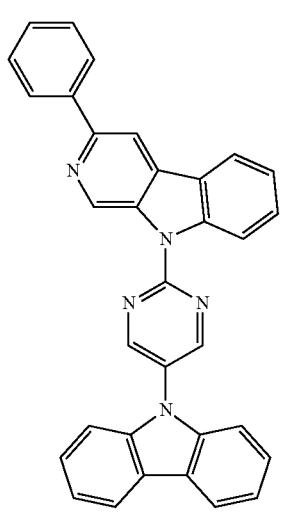
(A40)
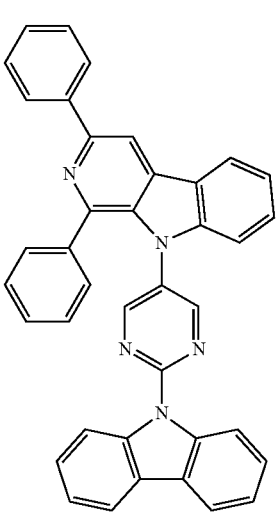
(A43)

(A44)
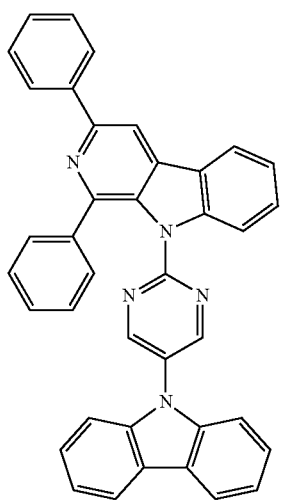
(A45)
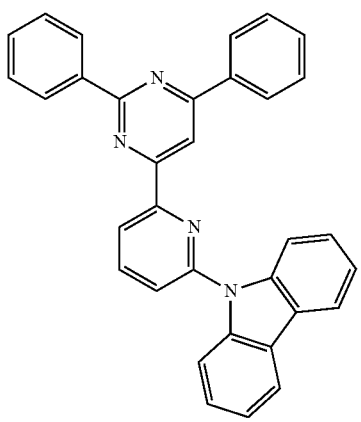
(A46)
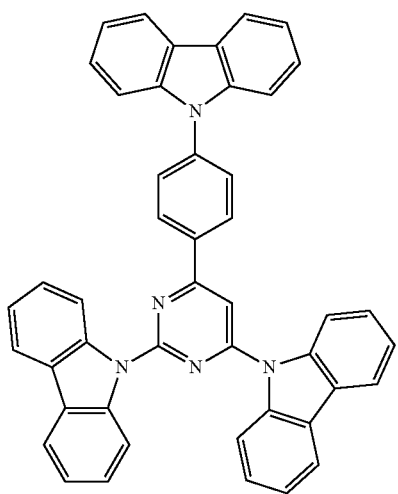
(A47)
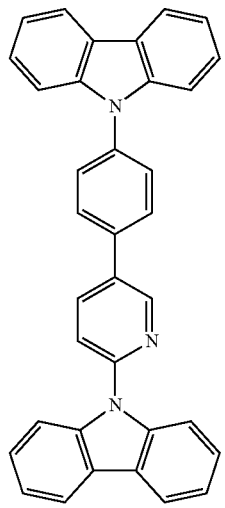
(A48)
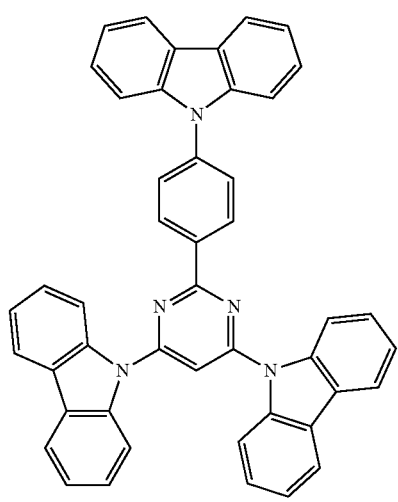
(A49)
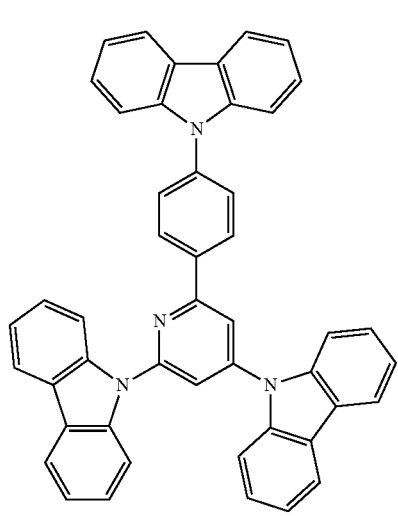

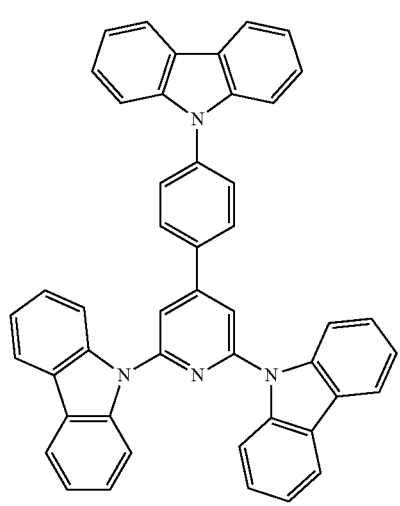 (A50)
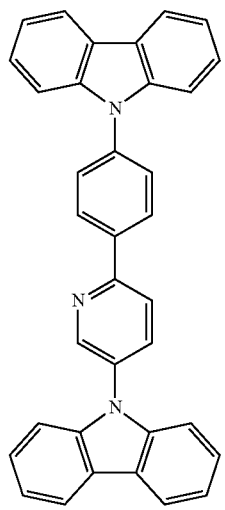 (A52)
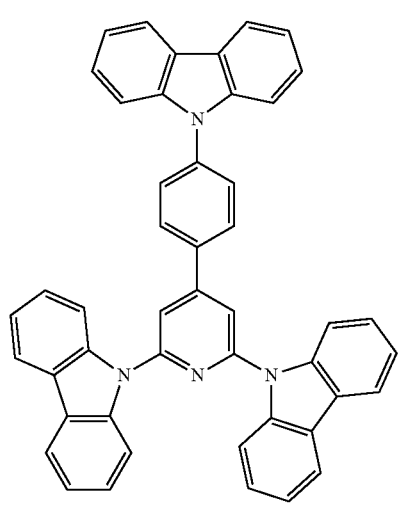 (A50)
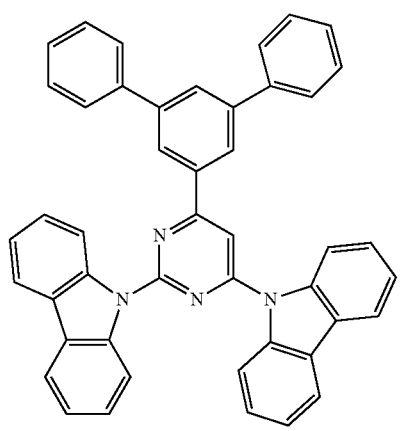 (A53)
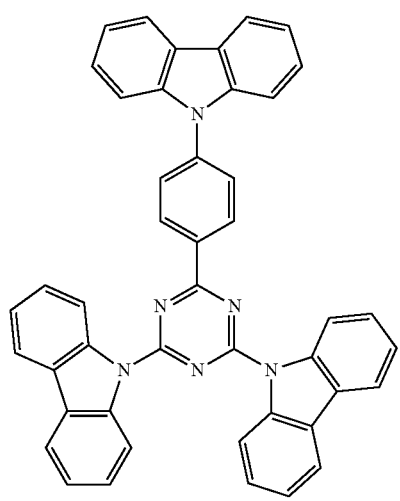 (A51)
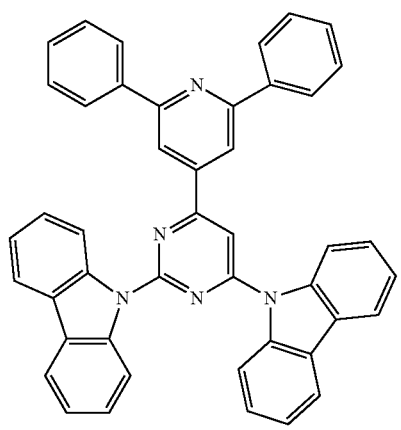 (A54)

(A55) 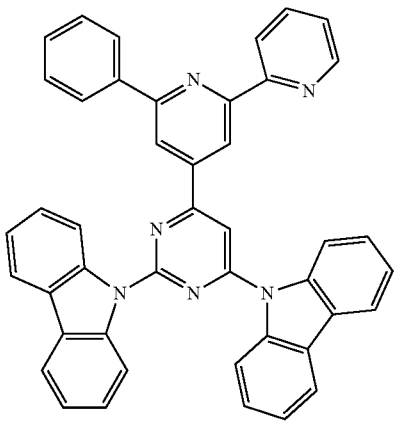

(A56) 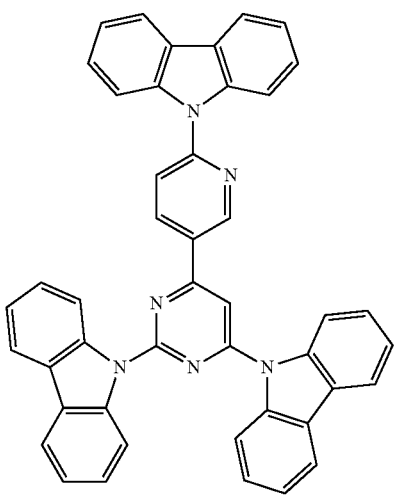

(A57) 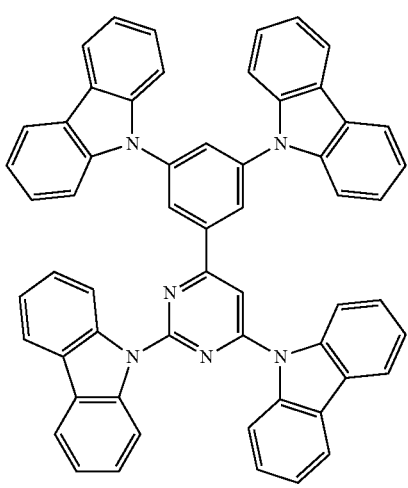

(A58) 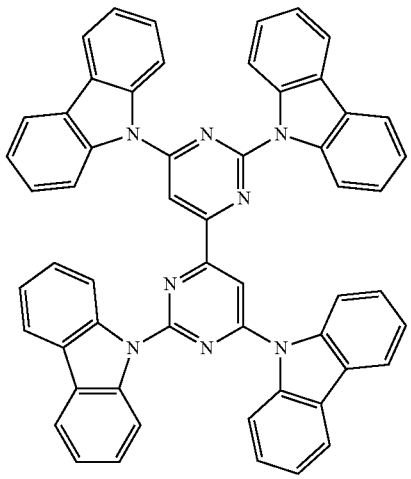

(A59) 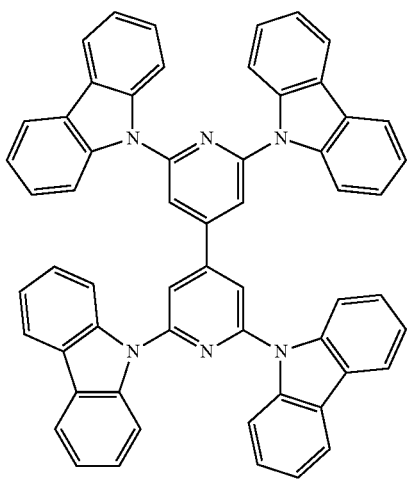

It is preferable that the singlet energy gap of the compound represented by general formula (1) of the present invention is 2.8 to 3.8 eV and more preferably 2.9 to 3.6 eV.

The organic EL device of the present invention comprises an anode, a cathode and an organic thin film layer comprising at least one layer sandwiched between the anode and the cathode, wherein at least one layer in the organic thin film layer contains the material for organic EL devices comprising the compound represented by the above general formula (1). It is preferable that the light emitting layer in the organic EL device of the present invention contains the material for organic EL devices comprising the compound represented by the above general formula (1).

The organic EL device of the present invention emits bluish light, and the purity of color of the emitted light is as excellent as (0.12, 0.11) to (0.16, 0.19). This property is exhibited since the material for organic EL devices comprising the compound represented by general formula (1) of the present invention has a great energy gap.

It is preferable that the organic EL device of the present invention emits light by a multiplet excitation which is the excitation to the triplet state or higher.

It is preferable that the material for organic EL devices is a host material of the organic EL device. The host material is a material into which holes and electrons can be injected and which has the function of transporting holes and electrons and emitting fluorescent light by recombination of holes and electrons.

The compound represented by general formula (1) in the present invention is useful also as the organic host material for phosphorescence devices since the singlet energy gap is as high as 2.8 to 3.8 eV and the triplet energy gap is as high as 2.5 to 3.3 eV.

The phosphorescence device is an organic device which comprises a substance emitting light based on the transition from the energy level in the triplet state to the energy level in the ground singlet state with a stronger intensity than those emitted from other substances, examples of which include phosphorescent substances such as organometallic complexes containing at least one metal selected from Groups 7 to 11 of the Periodic Table, and emits light under an electric field utilizing the so-called phosphorescence.

In the light emitting layer of the organic EL device, in general, the singlet exciton and the triplet exciton are contained in the formed excited molecules as a mixture, and it is reported that the triplet exciton is formed in a greater amount such that the ratio of the amount of the singlet exciton to the amount of the triplet exciton is 1:3. In conventional organic EL devices using the phosphorescence, the exciton contributing to the light emission is the singlet exciton, and the triplet exciton does not emit light. Therefore, the triplet exciton is ultimately consumed as heat, and the light is emitted by the singlet exciton which is formed in a smaller amount. Therefore, in these organic EL devices, the energy transferred to the triplet exciton causes a great loss in the energy generated by the recombination of holes and electrons.

In contrast, it is considered that, by using the material of the present invention for the phosphorescence device, the efficiency of light emission three times as great as that of a device using fluorescence can be obtained since the triplet exciton can be used for the emission of light. It is also considered that, when the compound of the present invention is used for the light emitting layer of the phosphorescence device, an excited triplet level in an energy state higher than the excited triplet level of a phosphorescent organometallic complex comprising a metal selected from the Group 7 to 11 of the Periodic Table contained in the layer, is achieved;

the film having a more stable form is provided; the glass transition temperature is higher (Tg: 80 to 160° C.); holes and/or electrons are efficiently transported; the compound is electrochemically and chemically stable; and the formation of impurities which may work as a trap or cause loss in the light emission is suppressed during the preparation and the use.

The hole transporting layer, the electron injecting layer or the hole barrier layer may contain the material of the present invention. A phosphorescent light emitting compound and the material of the present invention may be mixed and used in combination.

The organic EL device of the present invention comprises a cathode, an anode and an organic thin film layer comprising at least one layer and sandwiched between the cathode and the anode. When the organic thin film layer comprises a single layer, a light emitting layer is formed between the anode and the cathode. The light emitting layer contains a light emitting material and may further contain a hole injecting material for transporting holes injected from the anode to the light emitting material or an electron injecting material for transporting electrons injected from the cathode to the light emitting material. It is preferable that the light emitting material exhibits a very excellent quantum efficiency of fluorescence, has a great ability of transporting both holes and electrons and forms a uniform thin layer. Examples of the organic EL device of the multi-layer type include organic EL devices comprising a laminate having a multi-layer construction such as (the anode/the hole injecting layer/the light emitting layer/the cathode), (the anode/the light emitting layer/the electron injecting layer/the cathode) and (the anode/the hole injecting layer/the light emitting layer/the electron injecting layer/the cathode).

For the light emitting layer, in addition to the material of the present invention comprising the compound represented by general formula (1) of the present invention, conventional host materials, light emitting materials, doping materials, hole injecting materials and electron injecting materials and combinations of these materials may be used in combination, where necessary. By using a multi-layer structure for the organic EL device, decreases in the luminance and the life due to quenching can be prevented, and the luminance of emitted light and the efficiency of light emission can be improved with other doping materials. By using other doping materials contributing to the light emission of the phosphorescence in combination, the luminance of emitted light and the efficiency of light emission can be improved in comparison with those of conventional devices.

In the organic EL device of the present invention, the hole injecting layer, the light emitting layer and the electron injecting layer may each have a multi-layer structure. When the hole injecting layer has a multi-layer structure, the layer into which holes are injected from the electrode is called as a hole injecting layer, and the layer which receives holes from the hole injecting layer and transports holes to the light emitting layer is called as a hole transporting layer. Similarly, when the electron injecting layer has a multi-layer structure, the layer into which electron are injected from the electrode is called as an electron injecting layer, and the layer which receives electrons from the electron injecting layer and transports electrons to the light emitting layer is called as an electron transporting layer. The layers are selected in accordance with the energy levels of the material, heat resistance and adhesion with the organic thin film layers or the metal electrodes.

In the organic EL device of the present invention, the electron transporting layer and the hole transporting layer may contain the material for organic EL devices of the present invention which comprises the compound represented by general formula (1).

Examples of the light emitting material and the host material which can be used for the organic thin film layer in combination with the compound represented by general formula (1) include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenyl-butadiene, coumarine, oxadiazole, aldazine, bis-benzoxazoline, bisstyryl, pyrazine, cyclopentadiene, metal complexes of quinoline, metal complexes of aminoquinoline, metal complexes of benzoquinoline, imines, diphenyl- ethylene, vinylanthracene, diaminoanthracene, diaminocarbazole, pyrane, thiopyrane, polymethine, melocyanine, oxinoid compounds chelated with imidazole, quinacridone, rubrene, stilbene-based derivatives and fluorescent pigments. However, the light emitting material and the host material are not limited to the compounds described above.

As the light emitting material, phosphorescent organometallic complexes are preferable since the external quantum efficiency of the device can be improved. Examples of the metal in the phosphorescent organometallic complex include ruthenium, rhodium, palladium, silver, rhenium, osmium, iridium, platinum and gold. It is preferable that the organometallic complex is an organometallic compound represented by the following general formula (A):

[化15]

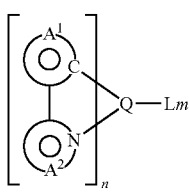
(A)

In the above general formula, A¹ represents a substituted or unsubstituted aromatic hydrocarbon cyclic group or aromatic heterocyclic group, which is preferably phenyl group, biphenyl group, naphthyl group, anthryl group, thienyl group, pyridyl group, quinolyl group or isoquinolyl group. Examples of the substituent include halogen atoms such as fluorine atom; alkyl groups having 1 to 30 carbon atoms such as methyl group and ethyl group; alkenyl groups such as vinyl group; alkoxycarbonyl groups having 1 to 30 carbon atoms such as methoxycarbonyl group and ethoxycarbonyl group; alkoxyl groups having 1 to 30 carbon atoms such as methoxyl group and ethoxyl group; aryloxyl groups such as phenoxyl group and benzyloxyl group; dialkylamino groups such as dimethylamino group and diethylamino group; acyl groups such as acetyl group; haloalkyl groups such as trifluoromethyl group; and cyano group.

A² represents a substituted or unsubstituted aromatic heterocyclic group having nitrogen atom as the atom forming the heterocyclic ring, which is preferably pyridyl group, pyrimidyl group, pyrazine group, triazine group, benzothiazole group, benzoxazole group, benzimidazole group, quinolyl group, isoquinolyl group, quinoxaline group or phenanthridine group. Examples of the substituent include the substituents described as the examples of the substituent for the group represented by A¹.

The ring having the group represented by A¹ and the ring having the group represented by A² may form one condensed ring. Examples of the condensed ring include 7,8-benzoquinoline group.

Q represents a metal selected from metals of Groups 7 to 11 of the Periodic Table, which is preferably ruthenium, rhodium, palladium, silver, rhenium, osmium, iridium, platinum or gold.

L represents a bidentate ligand, which is preferably selected from ligands of the β-diketone type such as acetylacetonates and pyromellitic acid.

m and n each represent an integer. When Q represents a divalent metal, n=2 and m=0. When Q represents a trivalent metal, n=3 and m=0 or n=2 and m=1.

Specific examples of the organometallic complex represented by the above general formula (A) are shown in the following. However, the organometallic complex is not limited to these compounds.

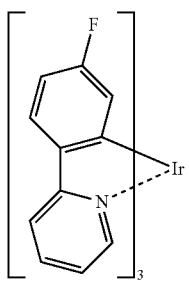
(K-1)

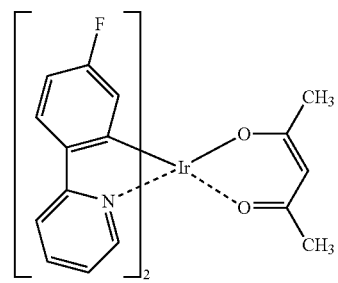
(K-2)

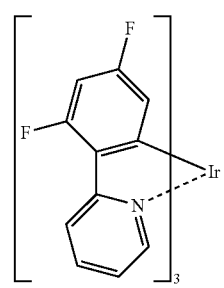
(K-3)

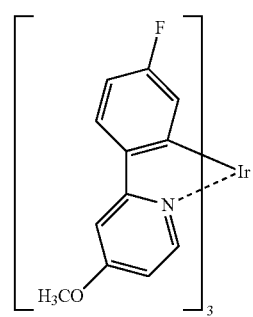
(K-4)

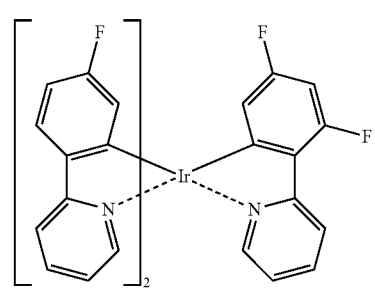
(K-5)

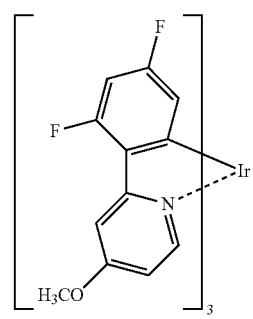
(K-6)

(K-7) 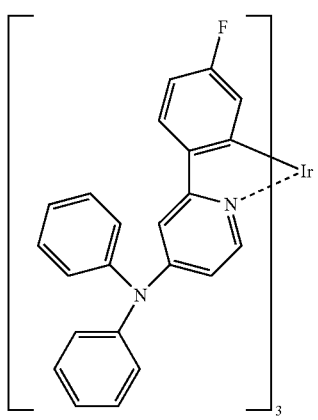
(K-8) 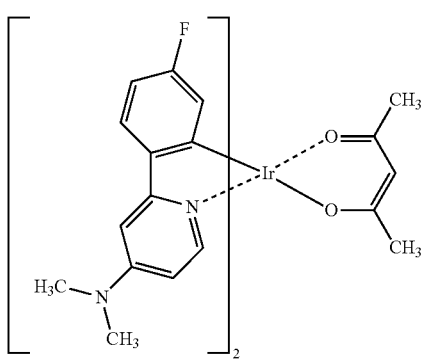
(K-9) 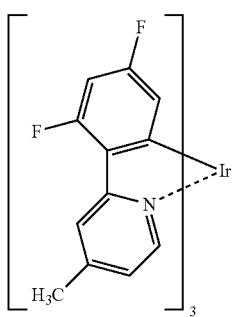
(K-10) 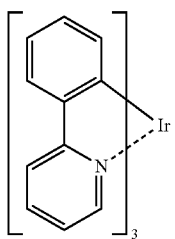
(K-11) 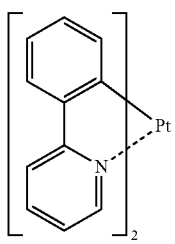
(K-12) 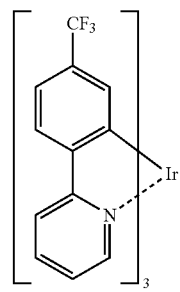
(K-13) 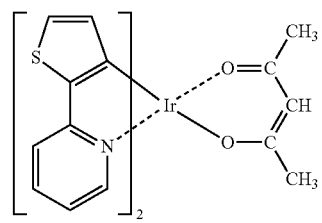
(K-14) 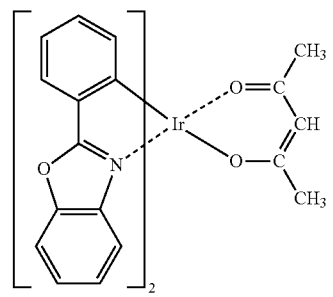
(K-15) 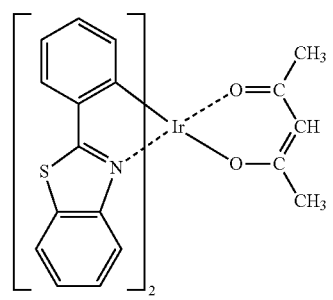
(K-16) 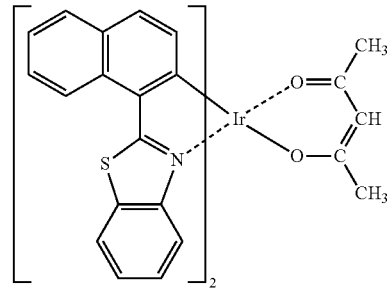

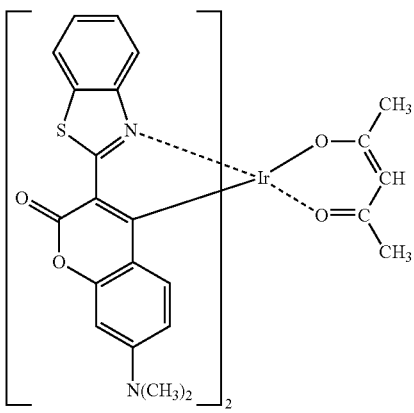
(K-17)

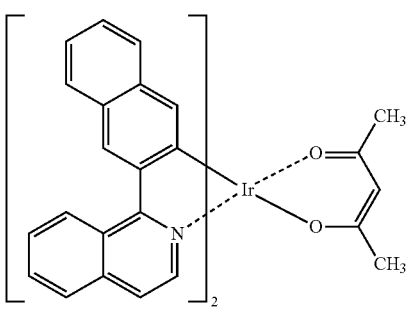
(K-18)

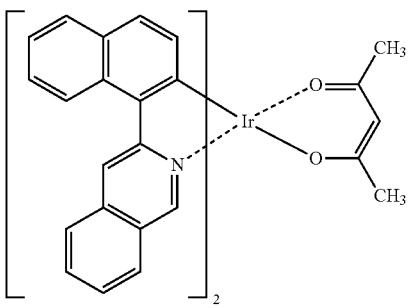
(K-19)

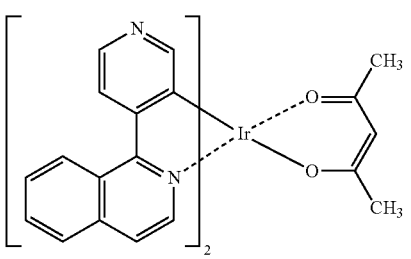
(K-20)

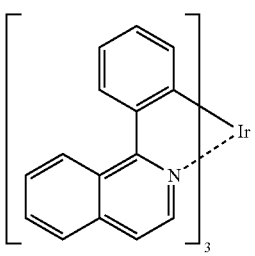
(K-21)

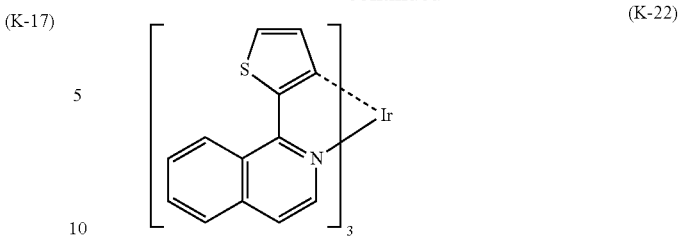
(K-22)

As the hole injecting material, compounds which have the ability to transport holes, exhibit the excellent effect of receiving holes injected from the anode and the excellent effect of injecting holes to the light emitting layer or the light emitting material, prevent transfer of excitons formed in the light emitting layer to the electron injecting layer or the electron injecting material and have the excellent ability of forming a thin film, are preferable. Examples of the hole injecting compound include phthalocyanine derivatives, naphthalocyanine derivatives, porphyrin derivatives, oxazoles, oxadiazoles, triazoles, imidazoles, imidazolones, imidazolethiones, pyrazolines, pyrazolones, tetrahydroimidazoles, oxazoles, oxadiazoles, hydrazones, acylhydrazones, polyarylalkanes, stilbene, butadiene, triphenylamine of the benzidine type, triphenylamine of the styrylamine type, triphenylamine of the diamine type, derivatives of the above compounds and macromolecular materials such as polyvinylcarbazoles, polysilanes and electrically conductive macromolecules. However, the hole injecting material is not limited to these materials.

Among these hole injecting materials, the more effective hole injecting materials are aromatic tertiary amine derivatives and phthalocyanine derivatives. Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methyl-phenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane and oligomers and polymers having the skeleton structure of these aromatic tertiary amines. However, the aromatic tertiary amine is not limited to these compounds. Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc. However the phthalocyanine derivative is not limited to these compounds.

As the electron injecting material, compounds which have the ability to transport electrons, exhibit the excellent effect of receiving electrons injected from the anode and the excellent effect of injecting electrons to the light emitting layer or the light emitting material, prevent transfer of excitons formed in the light emitting layer to the hole injecting layer and have the excellent ability of forming a thin film, are preferable. Examples of the electron injecting compound include fluorenone, anthraquinodimethane, diphenoquinone, thiopyrane dioxide, oxazoles, oxadiazoles, triazoles, imidazoles, perylenetetracarboxylic acid, quinoxaline, fluorenylidenemethane, anthraquinodimethane, anthrone and derivatives of these compounds. However, the electron injecting material is not limited to these compounds.

Among these electron injecting materials, the more effective electron injecting materials are metal complex compounds and five-membered derivatives having nitrogen. Examples of the metal complex compound include 8-hydroxyquinolinatolithium, bis(8-hydroxy- quinolinato)zinc, bis(8-hydroxyquinolinato)copper, bis(8-hydroxy-quinolinato) manganese, tris(8-hydroxyquinolinato)aluminum, tris(2-methyl-8-hydroxyquinolinato)aluminum, tris(8-hydroxyquinolinato)- gallium, bis(10-hydroxybenzo[h]quinolinato)beryllium, bis(10-hydroxy- benzo[h]quinolinato)zinc, bis(2-methyl-8-quinolinato)chlorogallium, bis(2-methyl-8-quinolinato)(o-cresolato)gallium, bis(2-methyl-8-quinolinato)-(1-naphtholato)aluminum and bis(2-methyl-8-quinolinato)(2-naphtholato)- gallium. However the electron injecting material is not limited to these compounds.

Oxazoles, thiazoles, oxadiazoles, thiadiazoles, triazoles and derivatives of these compounds are preferable as the five-membered derivative having nitrogen,. Specific examples of the five-membered derivative having nitrogen include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,5-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, the five-membered derivative having nitrogen is not limited to these compounds.

The property of charge injection can be improved by adding an electron-accepting compound to the hole injecting material and by adding an electron-donating compound to the electron injecting material.

As the electrically conductive material used for the anode of the organic EL device of the present invention, a material having a work function greater than 4 eV is suitable, and carbon, aluminum, vanadium, iron, cobalt, nickel, tungsten, silver, gold, platinum, palladium, alloys of these metals, metal oxides such as tin oxides and indium oxide used for ITO substrates and NESA substrates and organic electrically conductive resins such as polythiophene and polypyrrol are used. As the electrically conductive material used for the cathode, a material having a work function smaller than 4 eV is suitable, and magnesium, calcium, tin, lead, titanium, yttrium, lithium, ruthenium, manganese, aluminum and alloys of these metals are used. However, the electrically conductive material used for the cathode is not limited to these materials. Typical examples of the alloy include magnesium/silver, magnesium/indium and lithium/aluminum. However, the alloy is not limited to these alloys. The composition of the alloy is controlled by the temperature of the source of vaporization, the atmosphere and the degree of vacuum and a suitable composition is selected. The anode and the cathode may be formed with a structure having two or more layers, where necessary.

The organic EL device of the present invention may comprise an inorganic compound layer between at least one of the electrodes and the above organic thin film layer. Examples of the inorganic compound used for the inorganic compound layer include various types of oxides, nitrides and oxide nitrides such as alkali metal oxides, alkaline earth metal oxides, rare earth oxides, alkali metal halides, alkaline earth metal halides, rare earth halides, $SiO_x$, $AlO_x$, $SiN_x$, SiON, AlON, $GeO_x$, $LiO_x$, LiON, $TiO_x$, TiON, $TaO_x$, TaON, $TaN_x$ and C. In particular, as the component contacting the anode, $SiO_x$, $AlO_x$, $SiN_x$, SiON, AlON, $GeO_x$ and C are preferable since a stable interface layer of injection is formed. As the component contacting the cathode, LiF, $MgF_2$, $CaF_2$, $MgF_2$ and NaF are preferable.

In the organic EL device of the present invention, it is preferable that at least one surface is sufficiently transparent in the region of the wavelength of the light emitted by the device so that the light emission is achieved efficiently. It is preferable that the substrate is also transparent.

For the transparent electrode, the conditions in the vapor deposition or the sputtering are set so that the prescribed transparency is surely obtained using the above electrically conductive material. It is preferable that the electrode of the light emitting surface has a transmittance of light of 10% or greater. The substrate is not particularly limited as long as the substrate has the mechanical and thermal strength and is transparent. Examples of the substrate include glass substrates and transparent films of resins. Examples of the transparent film of a resin include films of polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketones, polysulfones, polyether sulfones, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyesters, polycarbonates, polyurethanes, polyimides, polyether imides, polyimides and polypropylene.

In the organic EL device of the present invention, it is possible that a protective layer is formed on the surface of the device or the entire device is covered with a silicone oil or a resin so that stability to the temperature, the humidity and the atmosphere is improved.

For the formation of each layer of the organic EL device of the present invention, any of the dry processes of film formation such as the vacuum vapor deposition, the sputtering, the plasma plating and the ion plating and the wet processes of film formation such as the spin coating, the dipping and the flow coating, can be applied. Although the thickness of each film is not particularly limited, it is necessary that the thickness of the film be set at a suitable value. When the thickness is excessively great, application of a greater voltage is necessary to obtain the same output of the light, and the efficiency of light emission decreases. When the thickness is excessively small, pin holes are formed, and sufficient light emission cannot be obtained even when an electric field is applied. In general, a thickness in the range of 5 nm to 10 μm is suitable and a thickness in the range of 10 nm to 0.2 μm is preferable.

When the wet process of film formation is used, the material forming each layer is dissolved or suspended in a suitable solvent such as ethanol, chloroform, tetrahydrofuran and dioxane, and a thin film is formed from the obtained solution or suspension. Any of the above solvents can be used. For any of the layers, suitable resins and additives may be used to improve the property for film formation and to prevent formation of pin holes in the film. Examples of the resin which can be used include insulating resins such as polystyrene, polycarbonates, polyarylates, polyesters, polyamides, polyurethanes, polysulfones, polymethyl methacrylate, polymethyl acrylate, cellulose and copolymer resins derived from these resins; photoconductive resins such as poly-N-vinylcarbazole and polysilanes; and electrically conductive resins such as polythiophene and polypyrrol. Examples of the additive include antioxidants, ultraviolet light absorbents and plasticizers.

As described above, by using the compound represented by general formula (1) for the organic thin film layer of the organic EL device of the present invention, the organic EL device emitting blue light with a high purity of color can be obtained. This organic EL device can be advantageously used for a photosensitive member for electronic photograph, a planar light emitting member such as a flat panel display of wall televisions, a back light of copiers, printers and liquid crystal displays, a light source for instruments, a display panel, a marker lamp and an accessory.

The present invention will be described more specifically with reference to examples in the following. However, the present invention is not limited to the examples.

The triplet energy gap and the singlet energy gap of a compound were measured in accordance with the following methods.

(1) Measurement of the Triplet Energy Gap

The lowest excited triplet energy level T1 was measured. The phosphorescence spectrum of a sample was measured (a 10 μmoles/liter EPA (diethyl ether:isopentane:ethanol=5:5:2 by volume) solution; 77K; a quartz cell; FLUOROLOG 11 manufactured by SPEX Company). A tangent line was drawn to the increasing line at the short wavelength side of the phosphorescence spectrum, and the wavelength (the end of light emission) at the intersection of the tangent line and the abscissa was obtained. The obtained wavelength was converted into the energy.

(2) Measurement of the Singlet Energy Gap

The excited singlet energy gap was measured. Using a toluene solution ($10^{-5}$ moles/liter) of a sample, the absorption spectrum was obtained by a spectrometer for absorption of ultraviolet and visible light manufactured by HITACHI Co. Ltd. A tangent line was drawn to the increasing line at the long wavelength side of the spectrum, and the wavelength (the end of absorption) at the intersection of the tangent line and the abscissa was obtained. The obtained wavelength was converted into the energy.

SYNTHESIS EXAMPLE 1

Synthesis of Compound (A2): 9-(2,6-dipyridyl-pyridin-4-yl)carbazole

The route of synthesis of Compound (A2) is shown in the following.

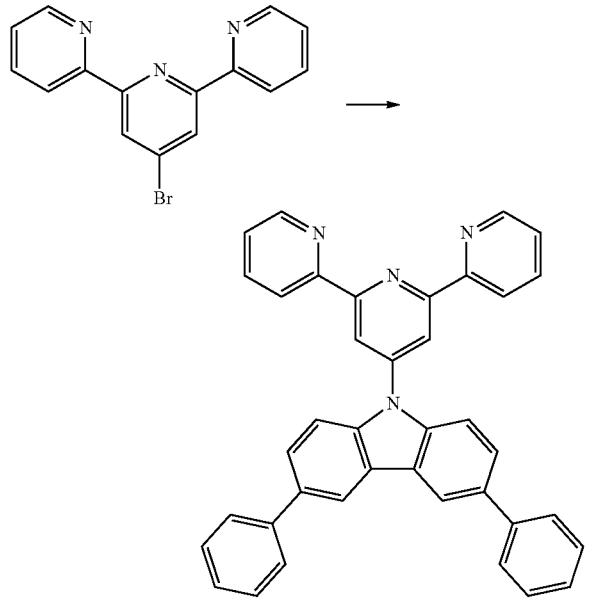

Under the atmosphere of argon, 2,6-dipyridyl-4-bromopyridine (9.4 g, 30 mmole), 3,6-diphenylcarbazole (9.6 g, 30 mmole), copper iodide (0.06 g, 0.32 mmole, 1% Cu), trans-1,2-cyclohexanediamine (0.4 ml, 3.3 mmole, 10 eq to Cu) and potassium phosphate (14 g, 66 mmole, 2.2 eq) were suspended in anhydrous dioxane (30 ml), and the resultant suspension was heated under the refluxing condition for 10 hours. The reaction mixture was filtered and washed with toluene. The filtrate was concentrated and, after purification in accordance with the column chromatography, a white solid substance (13.2 g, the yield: 80%) was obtained. It was confirmed in accordance with $^1$H-NMR and FD-MS (the field desorption mass analysis) that the product was Compound (A2) of the object compound. The result of the measurement by FD-MS is shown in the following.

FD-MS calcd. for $C_{39}H_{26}N_4$=550; found: m/z=550 (M$^+$, 100)

The singlet energy gap and the triplet energy gap of the obtained compound are shown in Table 1.

SYNTHESIS EXAMPLE 2

Synthesis of Compound (A14): 2-(2,6-dipyridyl-pyridin-4-yl)-5-(9-carbazolyl)pyrimidine The route of synthesis of Compound (A14) is shown in the following.

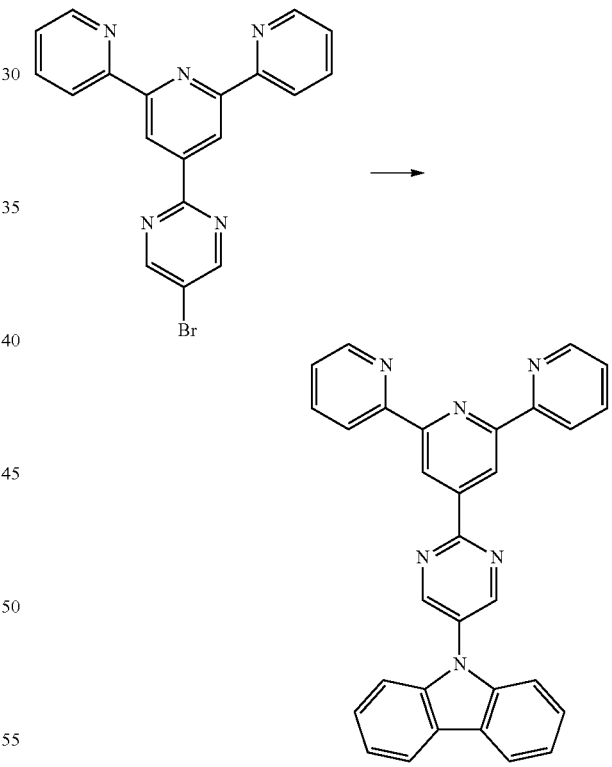

Under the atmosphere of argon, 2-(2,6-dipyridylpyridin-4-yl)-5-bromopyrimidine (12 g, 30 mmole), carbazole (5 g, 30 mmole), copper iodide (0.06 g, 0.32 mmole, 1% Cu), trans-1,2-cyclohexanediamine (0.4 ml, 3.3 mmole, 10 eq to Cu) and potassium phosphate (14 g, 66 mmole, 2.2 eq) were suspended in anhydrous dioxane (30 ml), and the resultant suspension was heated under the refluxing condition for 10 hours. The reaction mixture was filtered and washed with toluene. The filtrate was concentrated and, after purification in accordance with the column chromatography, a white solid substance (10.9 g, the yield: 76%) was obtained. It was confirmed in accordance with ¹H-NMR and FD-MS that the product was Compound (A14) of the object compound. The result of the measurement by FD-MS is shown in the following.

FD-MS calcd. for $C_{31}H_{20}N_6$=476; found: m/z=476 (M⁺, 100)

The singlet energy gap and the triplet energy gap of the obtained compound are shown in Table 1.

SYNTHESIS EXAMPLE 3

Synthesis of Compound (A33): 2,6-di(9-carbazolyl)-pyridine

The route of synthesis of Compound (A33) is shown in the following.

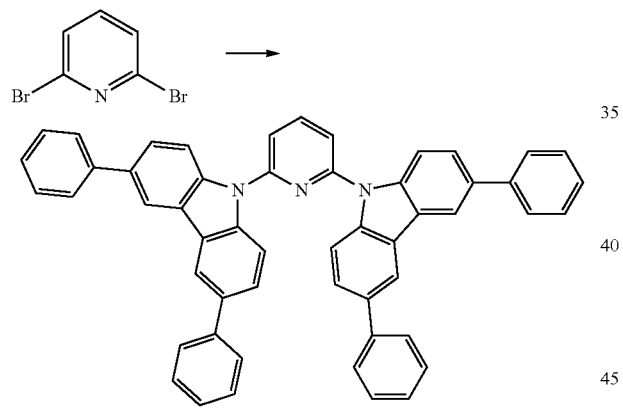

Under the atmosphere of argon, 2,6-dibromopyridine (2.4 g, 10 mmole), 3,6-diphenylcarbazole (9.6 g, 30 mmole), copper iodide (0.06 g, 0.32 mmole, 1% Cu), trans-1,2-cyclohexanediamine (0.4 ml, 3.3 mmole, 10 eq to Cu) and potassium phosphate (14 g, 66 mmole, 2.2 eq) were suspended in anhydrous dioxane (30 ml), and the resultant suspension was heated under the refluxing condition for 10 hours. The reaction mixture was filtered and washed with toluene. The filtrate was concentrated and, after purification in accordance with the column chromatography, a white solid substance (4.8 g, the yield: 67%) was obtained. It was confirmed in accordance with ¹H-NMR and FD-MS that the product was Compound (A33) of the object compound. The result of the measurement by FD-MS is shown in the following.

FD-MS calcd. for $C_{53}H_{35}N_3$=713; found: m/z=713 (M⁺, 100)

The singlet energy gap and the triplet energy gap of the obtained compound are shown in Table 1.

SYNTHESIS EXAMPLE 4

Synthesis of Compound (A45)

The route of synthesis of Compound (A45) is shown in the following.

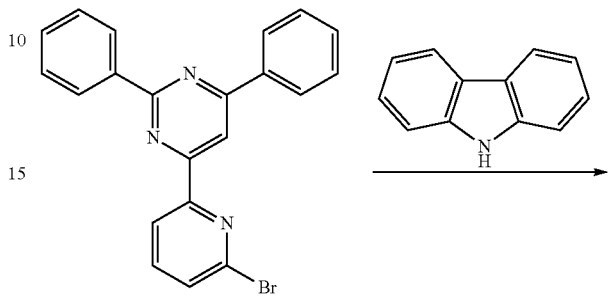

2-(2,4-Diphenylpyrimidin-6-yl)-6-bromopyridine (3.2 g, 8 mmole), carbazole (1.4 g, 9 mmole), copper iodide (0.08 g, 0.4 mmole) and potassium phosphate (3.7 g, 17 mmole) were suspended in 1,4-dioxane (16 ml), and trans-1,2-cyclohexanediamine (0.5 ml, 4 mmole) was added to the resultant suspension. The obtained suspension was heated under the refluxing condition for 15 hours under the atmosphere of argon. The reaction solution was cooled to the room temperature, and water was added. After extraction with methylene chloride, the obtained organic layer was washed with water and dried with anhydrous sodium sulfate. After the organic solvent was removed by distillation under a reduced pressure, 25 ml of ethyl acetate was added. The formed crystals were separated by filtration and washed with ethyl acetate, and crystals (2.3 g, the yield: 59%) were obtained. It was confirmed in accordance with 90 MHz ¹H-NMR and FD-MS that the obtained crystals were Compound (A45) of the object compound. The result of the measurement by FD-MS is shown in the following.

FD-MS calcd. for $C_{33}H_{22}N_4$=474; found: m/z=474 (M⁺, 100)

The singlet energy gap and the triplet energy gap of the obtained compound are shown in Table 1.

SYNTHESIS EXAMPLE 5

Synthesis of Compound (A46)

The route of synthesis of Compound (A46) is shown in the following.

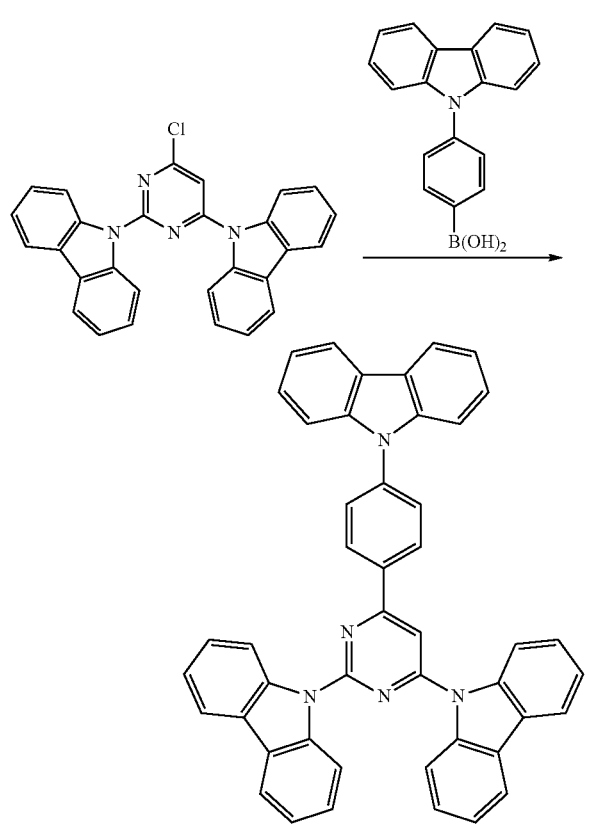

2,4-Dicarbazolyl-6-chloropyrimidine (2.5 g, 6 mmole), 4-carbazolyl-phenylboric acid (1.6 g, 6 mmole), copper iodide (0.08 g, 0.4 mmole) and tetrakis(triphenylphosphine)palladium (0.13 g, 0.1 mmole) were suspended in 1,2-dimethoxyethane (25 ml), and a solution prepared by dissolving sodium carbonate (1.8 ml, 17 mmole) in water (8 ml) was added to the resultant suspension. The obtained suspension was heated under the refluxing condition for 9 hours and 20 minutes. After the reaction solution was cooled to the room temperature, formed crystals were separated by filtration and washed with water, methanol and ethyl acetate, successively, and crude crystals (3.7 g) were obtained. The obtained crude crystals were purified by sublimation under a reduced pressure, and purified crystals (3.1 g, the yield: 85%) were obtained. It was confirmed in accordance with 90 MHz $_1$H-NMR and FD-MS that the obtained crystals were Compound (A46) of the object compound. The result of the measurement by FD-MS is shown in the following.

FD-MS calcd. for $C_{46}H_{29}N_5$=651; found: m/z=651 (M$^+$, 100)

The singlet energy gap and the triplet energy gap of the obtained compound are shown in Table 1.

SYNTHESIS EXAMPLE 6

Synthesis of Compound (A47)

The route of synthesis of Compound (A47) is shown in the following.

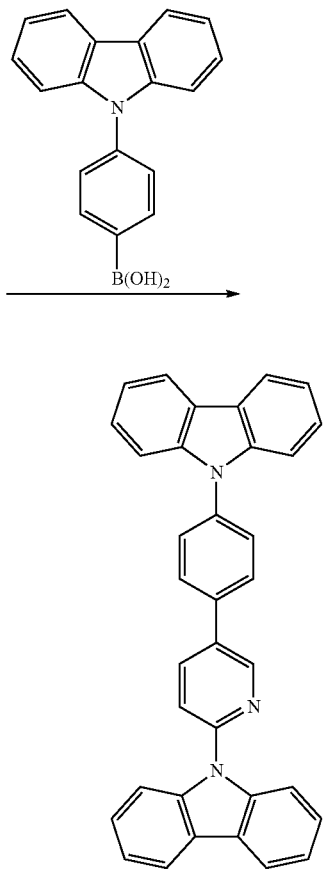

2-Carbazolyl-5-bromopyridine (1.9 g, 6 mmole), 4-carbazolylphenyl-boric acid (1.7 g, 6 mmole) and tetrakis(triphenylphosphine)palladium (0.14 g, 0.1 mmole) were suspended in 1,2-dimethoxyethane (18 ml), and a solution prepared by dissolving sodium carbonate (1.9 ml, 18 mmole) in water (9 ml) was added to the resultant suspension. The obtained suspension was heated under the refluxing condition for 9 hours and 15 minutes. After the reaction solution was cooled to the room temperature, formed crystals were separated by filtration and washed with water, methanol and ethyl acetate, successively, and crude crystals (2.9 g) were obtained. The formed crystals were purified by sublimation under a reduced pressure, and purified crystals (2.4 g, the yield: 84%) were obtained. It was confirmed in accordance with 90 MHz $^1$H-NMR and FD-MS that the obtained crystals were Compound (A47) of the object compound. The result of the measurement by FD-MS is shown in the following.

FD-MS calcd. for $C_{35}H_{23}N_3$=485; found: m/z=485 (M$^+$, 100)

The singlet energy gap and the triplet energy gap of the obtained compound are shown in Table 1.

TABLE 1

| | Compound | Singlet energy gap (eV) | Triplet energy gap (eV) |
|---|---|---|---|
| Synthesis Example 1 | A2 | 3.2 | 2.7 |
| Synthesis Example 2 | A14 | 3.2 | 2.8 |
| Synthesis Example 3 | A33 | 3.3 | 2.7 |
| Synthesis Example 4 | A45 | 3.2 | 2.8 |

TABLE 1-continued

| Compound | | Singlet energy gap (eV) | Triplet energy gap (eV) |
|---|---|---|---|
| Synthesis Example 5 | A46 | 3.3 | 2.8 |
| Synthesis Example 6 | A47 | 3.4 | 2.8 |

EXAMPLE 1

A glass substrate (manufactured by GEOMATEC Company) of 25 mm×75 mm×1.1 mm (thickness) having an ITO transparent electrode was ultrasonically cleaned in isopropyl alcohol for 5 minutes and then further cleaned by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis-(N,N'-diphenyl-4-aminophenyl)-N,N'-diphenyl-4,4'-diamino-1,1'-biphenyl (TPD232) having a thickness of 60 nm was formed in a manner such that the formed film covered the transparent electrode. The formed film of TPD232 worked as the hole injecting layer. On the formed film of TPD232, a film of 4,4'-bis[N-(1-naphthyl)-N-phenylamino]biphenyl (NPD) having a thickness of 20 nm was formed. The formed film of NPD worked as the hole transporting layer. On the formed film of NPD, a film of the above Compound (A2) having a thickness of 40 nm was formed by vapor deposition. At the same time, Compound (D1) shown in the following was vapor deposited in an amount such that the ratio of the amounts by weight of Compound (A2) to Compound (D1) was 40:3. Compound (D1) is a light emitting compound having a singlet energy as low as 2.79 eV so that blue light is emitted. The formed mixed film of Compound (A5) and Compound (D1) worked as the light emitting layer. On the film formed above, a film of BAlq shown in the following (Me means methyl group) having a thickness of 20 nm was formed. The film of BAlq worked as the electron injecting layer. Thereafter, Li (the source of lithium: manufactured by SAES GETTERS Company) as the reducing dopant and Alq were binary vapor deposited, and an Alq/Li film having a thickness of 10 nm was formed as the second electron injecting layer (the cathode). On the formed Alq/Li film, metallic aluminum was vapor deposited to form a metal cathode, and an organic EL device was prepared.

When a direct current voltage of 5.0 V was applied to the organic EL device prepared above, blue light was efficiently emitted at a luminance of 150 cd/m$^2$ and an efficiency of the light emission of 6.7 cd/A. The chromaticity coordinates were (0.15, 0.16), and the purity of color was excellent.

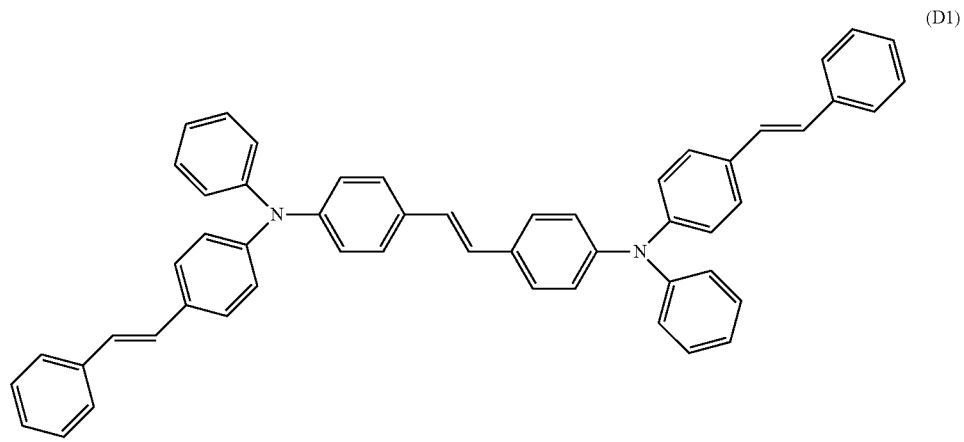

(D1)

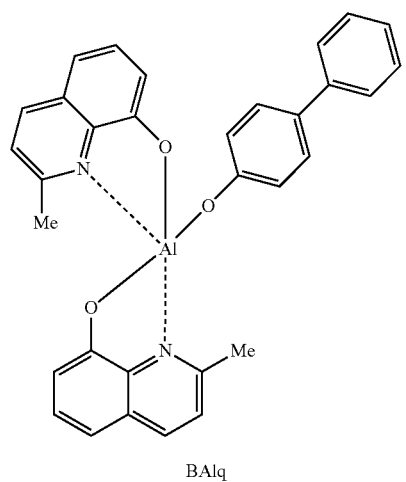

BAlq

EXAMPLES 2 TO 3

In accordance with the same procedures as those conducted in Example 1 except that compounds shown in Table 2 were used in place of Compound (A2), organic EL devices were prepared, and the voltage of the direct current, the luminance of the emitted light, the efficiency of the light emission, the color of the emitted light and the purity of color were measured. The results are shown in Table 2.

COMPARATIVE EXAMPLE 1

In accordance with the same procedures as those conducted in
Example 1 except that a conventional compound BCz shown in the following was used in place of Compound (A2), an organic EL device was prepared, and the voltage of the direct current, the luminance of the emitted light, the efficiency of the light emission, the color of the emitted light and the purity of color were measured. The results are shown in Table 2.

TABLE 2

BCz

| Organic host material of light emitting layer | Voltage (V) | Luminance of emitted light (cd/m²) | Efficiency of light emission (cd/A) | Color of emitted light | Chromaticity coordinates |
|---|---|---|---|---|---|
| Example 1 | A2 | 5.0 | 150 | 6.7 | blue | (0.15, 0.16) |
| Example 2 | A14 | 6.0 | 130 | 5.5 | blue | (0.14, 0.16) |
| Example 3 | A33 | 7.0 | 161 | 6.9 | blue | (0.15, 0.16) |
| Comparative Example 1 | BCz | 8.5 | 120 | 3.4 | blue | (0.14, 0.16) |

As shown in Table 2, in comparison with the organic EL device of Comparative Example 1 using the conventional compound BCz, the organic EL devices using the compounds of the present invention could be driven at lower voltages and emitted blue light in greater efficiencies. Since the energy gap of the compounds of the present invention is great, the light emitting molecule having a great energy gap could be mixed into the light emitting layer and used for the light emission.

EXAMPLE 4

A glass substrate of 25 mm×75 mm×1.1 mm (thickness) having an ITO transparent electrode was ultrasonically cleaned in isopropyl alcohol for 5 minutes and then further cleaned by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of copper phthalocyanine (CuPc shown in the following) having a thickness of 10 nm was formed in a manner such that the formed film covered the transparent electrode. The formed film of CuPc worked as the hole injecting layer. On the formed film of CuPc, a film of 4,4'-bis[N-(1-naphthyl)-N-phenylamino]biphenyl (α-NPD shown in the following) having a thickness of 30 nm was formed. The formed film of α-NPD worked as the hole transporting layer. On the formed film of α-NPD, a film of the above Compound (A46) as the host material having a thickness of 30 nm was formed by vapor deposition, and the light emitting layer was formed. At the same time, tris(2-phenylpyridine)iridium (Ir(ppy)$_3$ shown in the following) as the phosphorescent Ir metal complex dopant was added. The concentration of Ir(ppy)$_3$ in the light emitting layer was set at 5% by weight. This layer worked as the light emitting layer. On the film formed above, a film of (1,1'-bisphenyl)-4-olato)bis-(2-methyl-8-quinolinolato)aluminum (BAlq) having a thickness of 10 nm was formed. The BAlq film worked as the hole barrier layer. On the film formed above, a film of an aluminum complex of 8-hydroxyquinoline (Alq shown in the following) having a thickness of 40 nm was formed. The Alq film worked as the electron injecting layer. Thereafter, LiF as the alkali metal halide was vapor deposited in an amount such that the formed film had a thickness of 0.2 nm, and then aluminum was vapor deposited in an amount such that the formed film had a thickness of 150 nm. The formed Alq/Li film worked as the cathode. Thus, an organic EL device was prepared.

When the obtained device was tested by passing an electric current, green light having a luminance of 100 cd/m² was emitted with the efficiency of the light emission of 44.5 cd/A at a voltage of 5.5 V and a current density of 0.22 mA/cm². The chromaticity coordinates were (0.32, 0.61).

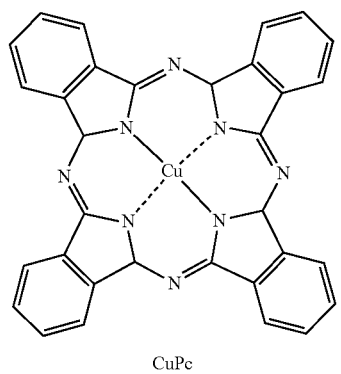

CuPc

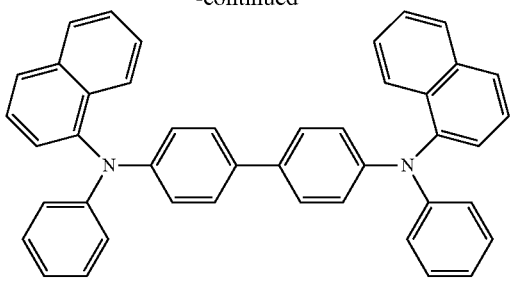

α-NPD

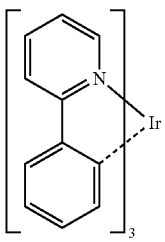

Ir(ppy)3

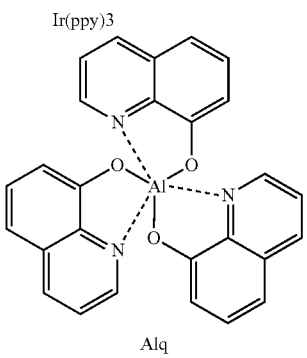

Alq

EXAMPLE 5

In accordance with the same procedures as those conducted in Example 4 except that Compound (A45) was used as the host material in the light emitting layer in place of Compound (A46), an organic EL device were prepared, and the voltage, the current density, the luminance of the emitted light, the efficiency of the light emission and the chromaticity were measured. The results are shown in Table 3.

COMPARATIVE EXAMPLE 2

In accordance with the same procedures as those conducted in Example 4 except that a conventional compound BCz shown above was used as the host material in the light emitting layer in place of Compound (A46), an organic EL device was prepared, and the voltage, the current density, the luminance of the emitted light, the efficiency of the light emission and the chromaticity were measured. The results are shown in Table 3.

COMPARATIVE EXAMPLE 3

In accordance with the same procedures as those conducted in Example 4 except that Compound (A-10) shown in the following which is described in United States Patent Application Laid-Open No. 2002-0028329A1 was used as the host material in the light emitting layer in place of Compound (A46), an organic EL device was prepared and the voltage, the current density, the luminance of the emitted light, the efficiency of the light emission and the chromaticity were measured. The results are shown in Table 3.

TABLE 3

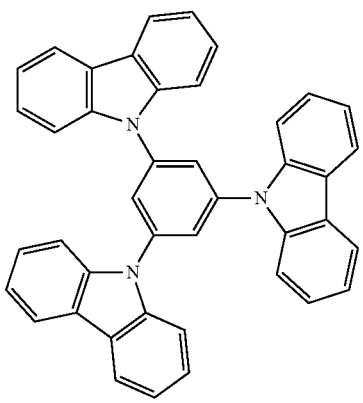

A-10

| | Organic host material in light emitting layer | Triplet energy gap (eV) | Singlet energy gap (eV) |
|---|---|---|---|
| Example 4 | A46 | 2.8 | 3.3 |
| Example 5 | A45 | 2.8 | 3.2 |
| Comparative Example 2 | BCz | 2.8 | 3.6 |
| Comparative Example 3 | A-10 | 3.1 | 3.7 |

TABLE 3-continued

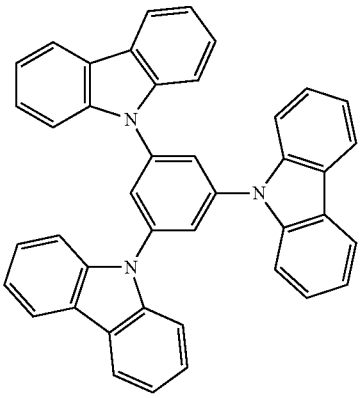 [SMILES: c1ccc2c(c1)c1ccccc1n2-c1cc(-n2c3ccccc3c3ccccc32)cc(-n2c3ccccc3c3ccccc32)c1]

A-10

|  | Voltage (V) | Current density (mA/cm²) | Luminance of emitted light (cd/m²) | Efficiency of light emission (cd/A) | Chromaticity coordinates (x, y) |
|---|---|---|---|---|---|
| Example 4 | 5.5 | 0.22 | 100 | 44.5 | (0.32, 0.61) |
| Example 5 | 5.7 | 0.23 | 97 | 41.8 | (0.32, 0.61) |
| Comparative Example 2 | 5.4 | 0.31 | 101 | 32.6 | (0.32, 0.61) |
| Comparative Example 3 | 5.9 | 0.32 | 100 | 31.8 | (0.32, 0.61) |

As shown in Table 3, in comparison with the organic EL devices of Comparative Examples 2 and 3 using conventional compounds (BCz and A-10), the organic EL devices using the compounds of the present invention emitted green light in greater efficiencies. Since the energy gap of the compounds of the present invention was great, the light emitting molecules having great energy gaps could be mixed into the light emitting layer and used for the light emission.

EXAMPLE 6

A glass substrate of 25 mm x 75 mm x 1.1 mm (thickness) having an ITO transparent electrode was ultrasonically cleaned in isopropyl alcohol for 5 minutes and then further cleaned by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of phthalocyanine copper (CuPc) having a thickness of 10 nm was formed in a manner such that the formed film covered the transparent electrode. The formed film of CuPc worked as the hole injecting layer. On the formed film of CuPc, a film of 1,1'-bis[4-N,N-di(para-tolyl)amino-phenyl]cyclohexane (TPAC shown in the following) having a thickness of 30 nm was formed. The formed film of TPAC worked as the hole transporting layer. On the formed film of TPAC, a film of the above Compound (A46) having a thickness of 30 nm was formed by vapor deposition, and the light emitting layer was formed. At the same time, Ir bis[(4,6-difluorophenyl)pyridinato-N,C²']picolinate (FIrpic shown in the following) as the phosphorescent Ir metal complex was added. The concentration of FIrpic in the light emitting layer was set at 7% by weight. The formed film worked as the light emitting layer. On the film formed above, a film of the aluminum complex of 8-hydroxyquinoline (Alq) having a thickness of 30 nm was formed. The film of Alq worked as the electron injecting layer. Thereafter, Li as the alkali metal halide was vapor deposited, and a film having a thickness of 0.2 nm was formed. Then, aluminum was vapor deposited, and a film having a thickness of 150 nm was formed. The formed Alq/Li film worked as the cathode. An organic EL device was prepared as described above.

When the obtained device was tested by passing an electric current, blue light having a luminance of 99 cd/m² was emitted with the efficiency of the light emission of 22.4 cd/A at a voltage of 6.4 V and a current density of 0.44 mA/cm². The chromaticity coordinates were (0.17, 0.39).

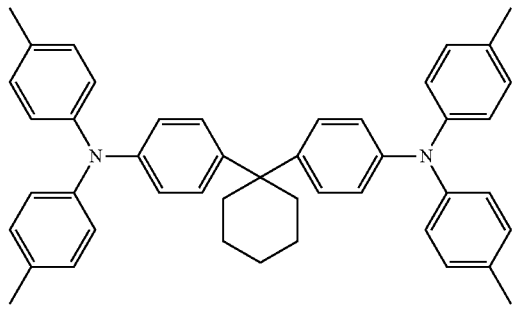

TPAC

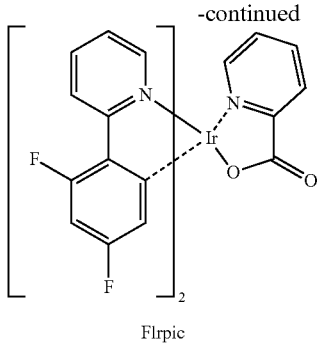

Flrpic

EXAMPLE 7

In accordance with the same procedures as those conducted in Example 6 except that Compound (A45) was used as the host material in the light emitting layer in place of Compound (A46), an organic EL devices was prepared, and the voltage, the current density, the luminance of the emitted light, the efficiency of the light emission, the chromaticity were measured. The results are shown in Table 4.

COMPARATIVE EXAMPLE 4

In accordance with the same procedures as those conducted in Example 6 except that the above conventional compound BCz was used as the host material in the light emitting layer in place of Compound (A46), an organic EL devices was prepared, and the voltage, the current density, the luminance of the emitted light, the efficiency of the light emission, the chromaticity were measured. The results are shown in Table 4.

COMPARATIVE EXAMPLE 5

In accordance with the same procedures as those conducted in Comparative Example 4 except that α-NPD was used for the hole transporting layer in place of the compound (TPAC) and BAlq was used for the electron injecting layer in place of the compound Alq, an organic EL devices was prepared, and the voltage, the current density, the luminance of the emitted light, the efficiency of the light emission, the chromaticity were measured. The results are shown in Table 4.

TABLE 4

| | Organic host material in light emitting layer | Triplet energy gap (eV) | Singlet energy gap (eV) |
|---|---|---|---|
| Example 6 | A46 | 2.8 | 3.3 |
| Example 7 | A45 | 2.8 | 3.2 |
| Comparative Example 4 | BCz | 2.8 | 3.6 |
| Comparative Example 5 | BCz | 2.8 | 3.6 |

| | Voltage (V) | Current density (mA/cm$^2$) | Luminance of emitted light (cd/m$^2$) | Efficiency of light emission (cd/A) | Chromaticity coordinates (x, y) |
|---|---|---|---|---|---|
| Example 6 | 6.4 | 0.44 | 99 | 22.4 | (0.17, 0.39) |
| Example 7 | 6.8 | 0.55 | 99 | 18.2 | (0.17, 0.39) |
| Comparative Example 4 | 7.8 | 1.70 | 98 | 5.80 | (0.16, 0.37) |
| Comparative Example 5 | 7.6 | 1.09 | 99 | 9.15 | (0.17, 0.37) |

As shown in Table 4, in comparison with the organic EL devices of Comparative Examples using the conventional compound BCz, the organic EL devices using the compounds of the present invention could be driven at lower voltages and emitted blue light in greater efficiencies. Since the energy gap of the compound of the present invention was great, the light emitting molecules having great energy gaps could be mixed into the light emitting layer and used for the light emission.

Industrial Applicability

As described above in detail, by utilizing the material for organic electroluminescence devices comprising the compound represented by general formula (1) of the present invention, the organic electroluminescence device emitting blue light having an excellent purity of color at a high efficiency of light emission can be obtained. Therefore, the organic electroluminescence device of the present invention is very useful as the light source for various electronic instruments.

The invention claimed is:

1. A compound according to formula (1):

$$(Cz\text{-})_n M_m \tag{1}$$

wherein:
  each Cz is independently a substituted carbazolyl group or an unsubstituted carbazolyl group;
  each substituted carbazolyl group Cz independently comprises at least one substituent selected from a substituted aromatic group, an unsubstituted aromatic group, a substituted aromatic heterocyclic group, and an unsubstituted aromatic heterocyclic group;
  each M is independently a substituted pyrimidine, a substituted pyrazine, an unsubstituted pyrazine, a substituted aziridine, an unsubstituted aziridine, a substituted azaindolizine, an unsubstituted azaindolizine, a substituted isoindole, an unsubstituted isoindole, a substituted indazole, an unsubstituted indazole, a substituted purine, an unsubstituted purine, a substituted pteridine, an unsubstituted pteridine, a substituted β-carboline, an unsubstituted β-carboline, a substituted quinoxaline, an unsubstituted quinoxaline, a substituted quinazoline, an unsubstituted quinazoline, a substituted phenanthroline, an unsubstituted phenanthroline, a substituted phenazine, or an unsubstituted phenazine;
  each substituted group M independently comprises at least one substituent selected from a substituted aromatic group, an unsubstituted aromatic group, a substituted aromatic heterocyclic group, and an unsubstituted aromatic heterocyclic group;
  m is an integer of 1 to 3;
  n is an integer of 1 to 3; and
  at least one group M is bonded to at least one carbazolyl group Cz at a 9-position of the at least one carbazolyl group Cz.

2. The compound according to claim 1, wherein the compound is a compound according to any one of formulas (2), (3), and (5) to (8):

$$Cz\text{—}M \quad (m = n = 1) \tag{2}$$

-continued

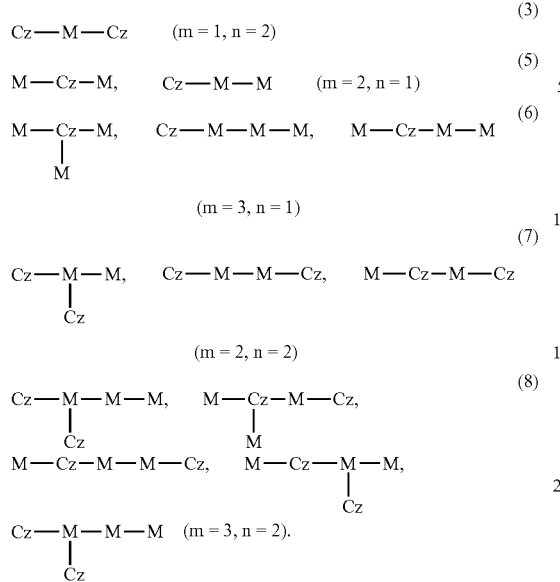

3. An organic electroluminescence device, comprising:
an anode;
a cathode; and
an organic thin film layer;
wherein:
the organic thin film layer is disposed between the anode and the cathode; and
the organic thin film layer comprises the compound according to claim 1.

4. The organic electroluminescence device according to claim 3, wherein:
the organic thin film layer comprises a light emitting layer; and
the light emitting layer comprises the compound according to formula (1).

5. The organic electroluminescence device according to claim 3, wherein:
the organic thin film layer comprises a light emitting layer;
the light emitting layer comprises a host material; and
the host material comprises the compound according to formula (1).

6. The organic electroluminescence device according to claim 3, wherein:
the organic thin film layer comprises an electron transporting layer; and
the electron transporting layer comprises the compound according to formula (1).

7. The compound according to claim 1, wherein a singlet energy gap of the compound is 2.8 to 3.8 eV.

8. The compound according to claim 1, wherein a singlet energy gap of the compound is 2.9 to 3.6 eV.

9. The compound according to claim 1, wherein a triplet energy gap of the compound is 2.5 to 3.3 eV.

10. The organic electroluminescent device according to claim 3, wherein the organic electroluminescent device emits bluish light.

11. The organic electroluminescent device according to claim 3, wherein the organic electroluminescent device emits light by multiplet excitation to a triplet state or higher.

12. An organic electroluminescence device, comprising:
an anode;
a cathode; and
an organic thin film layer;
wherein:
the organic thin film layer is disposed between the anode and the cathode; and
the organic thin film layer comprises a compound according to formula (1):

$$(Cz\text{-})_n M_m \tag{1}$$

wherein:
each Cz is independently a substituted carbazolyl group or an unsubstituted carbazolyl group;
each substituted carbazolyl group Cz independently comprises at least one substituent selected from a substituted aromatic group, an unsubstituted aromatic group, a substituted aromatic heterocyclic group, and an unsubstituted aromatic heterocyclic group;
each M is independently a substituted pyridine, an unsubstituted pyridine, a substituted pyrimidine, an unsubstituted pyrimidine, a substituted pyrazine, an unsubstituted pyrazine, a substituted aziridine, an unsubstituted aziridine, a substituted azaindolizine, an unsubstituted azaindolizine, a substituted isoindole, an unsubstituted isoindole, a substituted indazole, an unsubstituted indazole, a substituted purine, an unsubstituted purine, a substituted pteridine, an unsubstituted pteridine, a substituted β-carboline, an unsubstituted β-carboline, a substituted quinoxaline, an unsubstituted quinoxaline, a substituted quinazoline, an unsubstituted quinazoline, a substituted phenanthroline, an unsubstituted phenanthroline, a substituted phenazine, or an unsubstituted phenazine;
each substituted group M independently comprises at least one substituent selected from a substituted aromatic group, an unsubstituted aromatic group, a substituted aromatic heterocyclic group, and an unsubstituted aromatic heterocyclic group;
m is an integer of 1 to 3;
n is an integer of 1 to 3; and
at least one group M is bonded to at least one carbazolyl group Cz at a 9-position of the at least one carbazolyl group Cz.

13. The organic electroluminescence device according to claim 12, wherein the compound is a compound according to any one of formulas (2), (3), and (5) to (8):

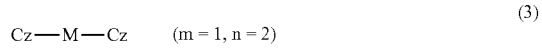

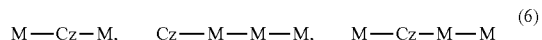

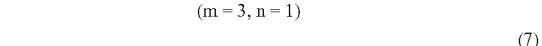

-continued $$M-Cz-M-M-Cz, \quad M-Cz-M-M,$$
$$\phantom{M-Cz-M-M-Cz, \quad M-Cz-M}|$$
$$\phantom{M-Cz-M-M-Cz, \quad M-Cz-M}Cz$$

$$Cz-M-M-M \quad (m=3, n=2).$$
$$|$$
$$Cz$$

14. The organic electroluminescence device according to claim 12, wherein:
the organic thin film layer comprises a light emitting layer; and
the light emitting layer comprises the compound according to formula (1).

15. The organic electroluminescence device according to claim 12, wherein:
the organic thin film layer comprises a light emitting layer;
the light emitting layer comprises a host material; and
the host material comprises the compound according to formula (1).

16. The organic electroluminescence device according to claim 12, wherein:
the organic thin film layer comprises an electron transporting layer; and
the electron transporting layer comprises the compound according to formula (1).

17. The organic electroluminescence device according to claim 12, wherein at least one group M is a substituted pyrimidine, an unsubstituted pyrimidine, a substituted pyrazine, an unsubstituted pyrazine, a substituted aziridine, an unsubstituted aziridine, a substituted azaindolizine, an unsubstituted azaindolizine, a substituted isoindole, an unsubstituted isoindole, a substituted indazole, an unsubstituted indazole, a substituted purine, an unsubstituted purine, a substituted pteridine, an unsubstituted pteridine, a substituted β-carboline, an unsubstituted β-carboline, a substituted quinoxaline, an unsubstituted quinoxaline, a substituted quinazoline, an unsubstituted quinazoline, a substituted phenanthroline, an unsubstituted phenanthroline, a substituted phenazine, or an unsubstituted phenazine.

18. The organic electroluminescence device according to claim 12, wherein a singlet energy gap of the compound is 2.8 to 3.8 eV.

19. The organic electroluminescence device according to claim 12, wherein a singlet energy gap of the compound is 2.9 to 3.6 eV.

20. The organic electroluminescence device according to claim 12, wherein a triplet energy gap of the compound is 2.5 to 3.3 eV.

21. The organic electroluminescent device according to claim 12, wherein the organic electroluminescent device emits bluish light.

22. The organic electroluminescent device according to claim 12, wherein the organic electroluminescent device emits light by multiplet excitation to a triplet state or higher.

* * * * *